United States Patent
Strominger et al.

(10) Patent No.: US 9,028,835 B2
(45) Date of Patent: *May 12, 2015

(54) COPOLYMERS FOR SUPPRESSION OF AUTOIMMUNE DISEASES, AND METHODS OF USE

(75) Inventors: Jack L. Strominger, Cambridge, MA (US); Masha Fridkis-Hareli, Sudbury, MA (US)

(73) Assignee: President and Fellows of Harvard College, Cambridge, MA (US)

(*) Notice: Subject to any disclaimer, the term of this patent is extended or adjusted under 35 U.S.C. 154(b) by 257 days.

This patent is subject to a terminal disclaimer.

(21) Appl. No.: 13/181,079

(22) Filed: Jul. 12, 2011

(65) Prior Publication Data

US 2011/0286959 A1 Nov. 24, 2011

Related U.S. Application Data

(60) Division of application No. 12/005,239, filed on Dec. 26, 2007, now Pat. No. 8,017,125, which is a division of application No. 10/406,783, filed on Apr. 3, 2003, now Pat. No. 7,381,790, which is a continuation-in-part of application No. PCT/US02/31399, filed on Oct. 3, 2002.

(60) Provisional application No. 60/326,705, filed on Oct. 3, 2001.

(51) Int. Cl.
| | |
|---|---|
| C07K 14/00 | (2006.01) |
| A61K 38/20 | (2006.01) |
| A61K 38/21 | (2006.01) |
| A61K 38/02 | (2006.01) |
| A61K 39/00 | (2006.01) |

(52) U.S. Cl.
CPC ............ *C07K 14/001* (2013.01); *A61K 38/2026* (2013.01); *A61K 38/2066* (2013.01); *A61K 38/215* (2013.01); *A61K 38/02* (2013.01); *Y10S 435/975* (2013.01)

(58) Field of Classification Search
None
See application file for complete search history.

(56) References Cited

U.S. PATENT DOCUMENTS 6,750,321 B1 * 6/2004 Chen et al. .................... 530/317

FOREIGN PATENT DOCUMENTS

| EP | WO96/01274 A1 | 1/1996 |
| WO | WO 00/05250 A1 * | 2/2000 |

OTHER PUBLICATIONS

Dore-Duffy et al (J. Clin. Invest. 1979, 63: 154-157).*

* cited by examiner

*Primary Examiner* — Gerald R Ewoldt
*Assistant Examiner* — Marianne Dibrino
(74) *Attorney, Agent, or Firm* — Lawson & Weitzen LLP; Sonia K. Guterman; Anna B. Stanford

(57) ABSTRACT

Random three- and four-amino acid copolymers having lengths of 14-, 35- and 50-amino acid residues are provided. The random copolymers have amino acids alanine, lysine and one or more of the hydrophobic amino acids valine, phenylalanine, tryptophan and tyrosine. Random three-amino acid copolymer FAK efficiently suppressed EAE induced in SJL/J (H-2S) mice with the encephalitogenic epitope PLP 139-151. Random four-amino acid copolymers VYAK and tryptophan-containing VWAK were efficacious in alleviating severity and duration of symptoms of EAE induced by MBP 85-99 (SEQ ID NO:2), in a humanized mouse model expressing genes for both an HLA-DR-2 linked to multiple sclerosis (MS) in humans and for a T cell receptor from an MS patient.

6 Claims, 13 Drawing Sheets

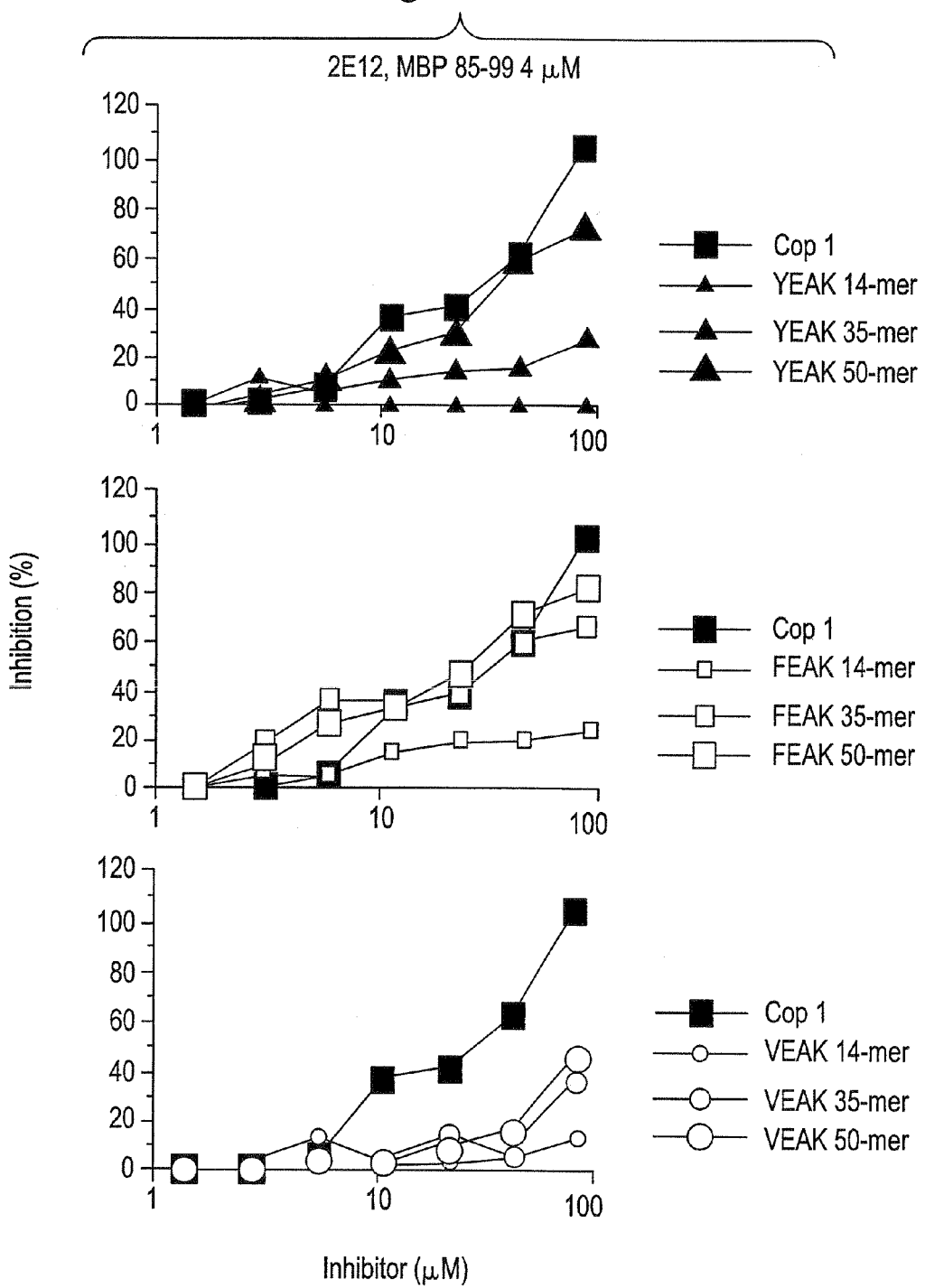

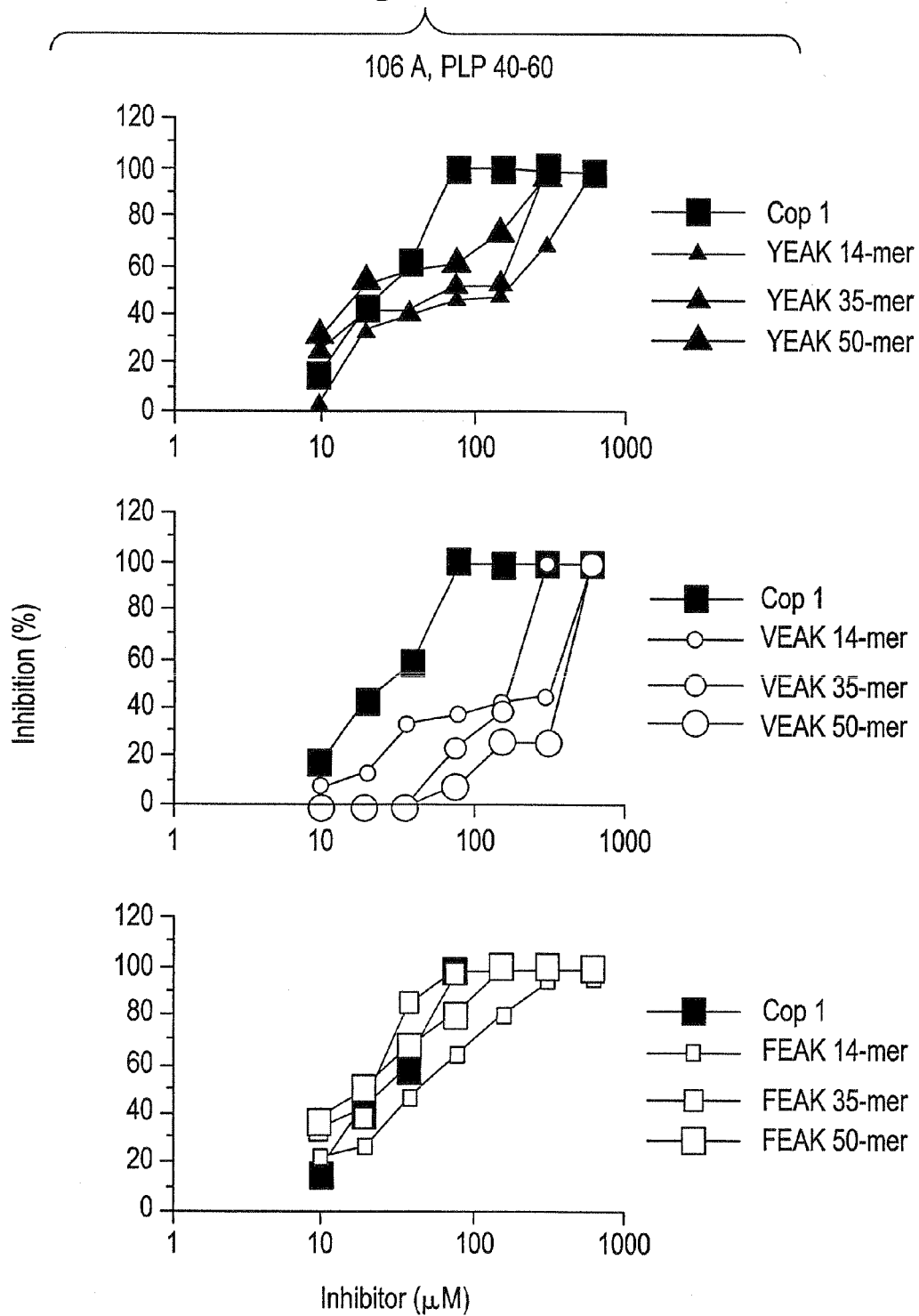

hPLP/1, PLP 139-151 hPLP/c4, PLP 139-151

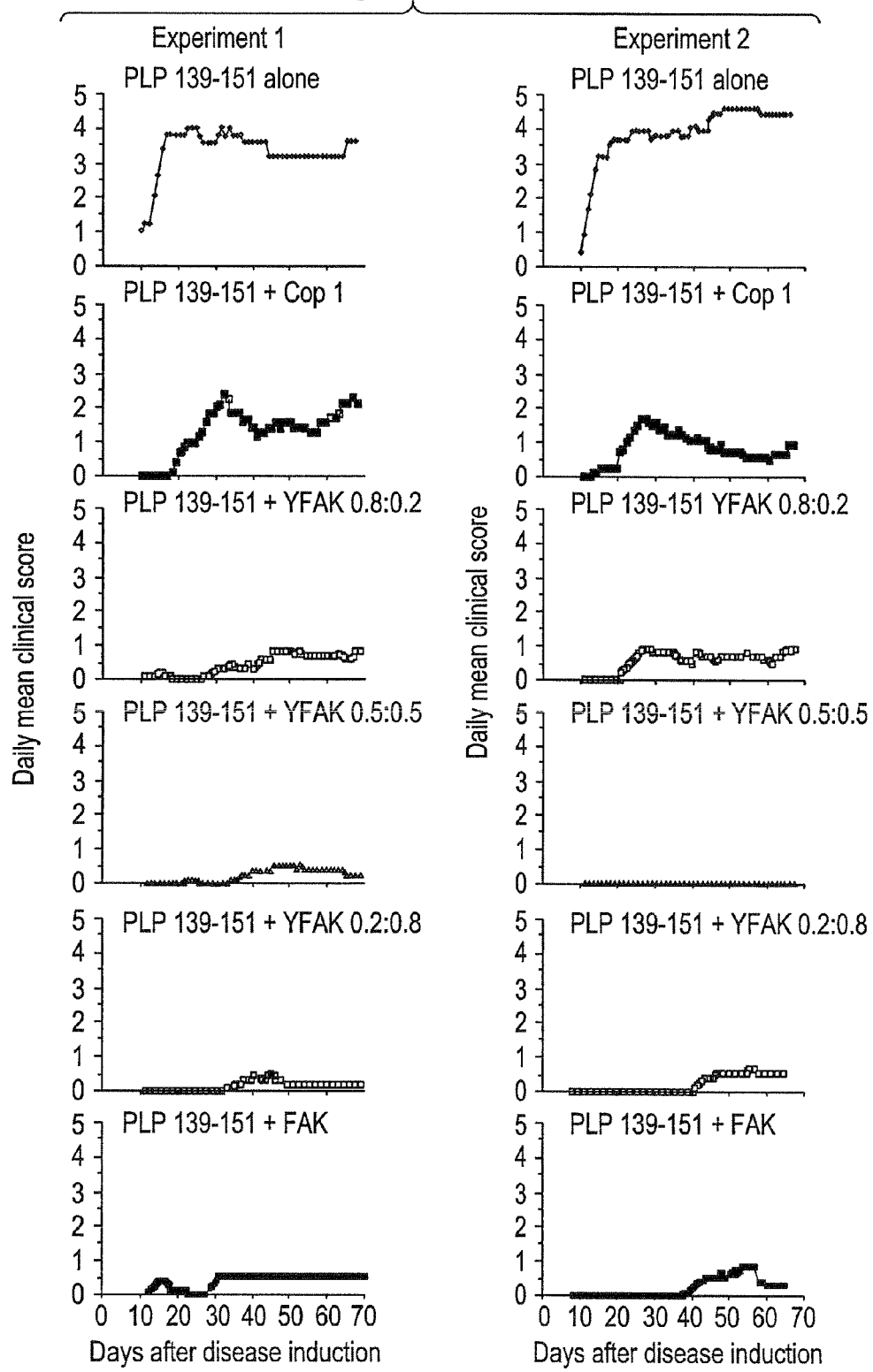

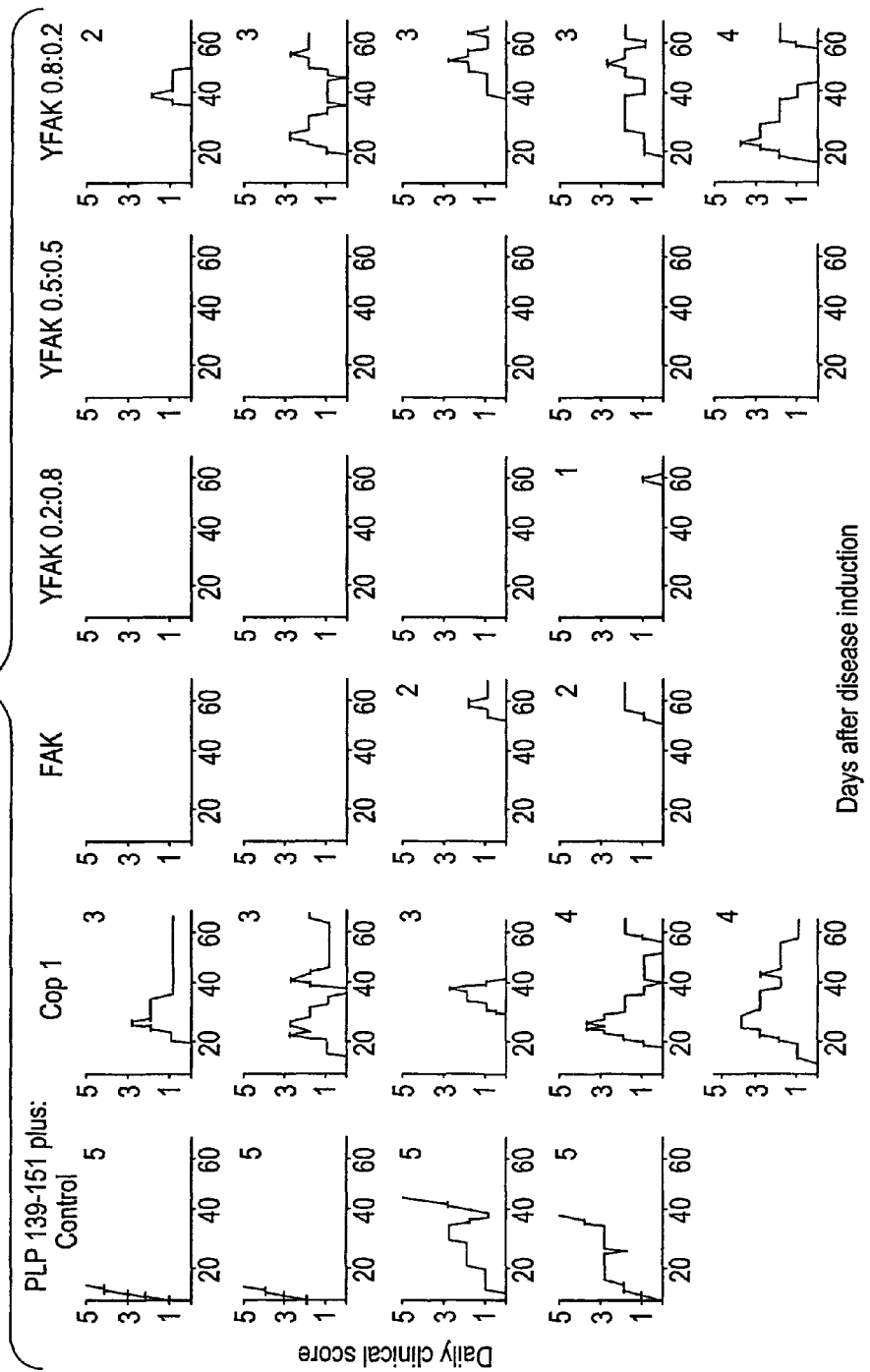

SEQUENCE LISTING

<160> NUMBER OF SEQ ID NOS: 5

<210> SEQ ID NO 1
<211> LENGTH: 15
<212> TYPE: PRT
<213> ORGANISM: Human
<220> FEATURE:
<221> NAME/KEY: DOMAIN
<222> LOCATION: (86)...(100)
<223> OTHER INFORMATION: myelin basic protein

<400> SEQUENCE: 1

Asn Pro Val Val His Phe Phe Lys Asn Ile Val Thr Pro Arg Thr
 1               5                   10                  15

<210> SEQ ID NO 2
<211> LENGTH: 15
<212> TYPE: PRT
<213> ORGANISM: Human
<220> FEATURE:
<221> NAME/KEY: DOMAIN
<222> LOCATION: (85)...(99)
<223> OTHER INFORMATION: myelin basic protein

<400> SEQUENCE: 2

Glu Asn Pro Val Val His Phe Phe Lys Asn Ile Val Thr Pro Arg
 1               5                   10                  15

<210> SEQ ID NO 3
<211> LENGTH: 21
<212> TYPE: PRT
<213> ORGANISM: Human
<220> FEATURE:
<221> NAME/KEY: DOMAIN
<222> LOCATION: (40)...(60)
<223> OTHER INFORMATION: proteolipid protein

<400> SEQUENCE: 3

Thr Gly Thr Glu Lys Leu Ile Glu Thr Tyr Phe Ser Lys Asn Tyr Gln
 1               5                   10                  15

Asp Tyr Glu Tyr Leu
            20

<210> SEQ ID NO 4
<211> LENGTH: 13
<212> TYPE: PRT
<213> ORGANISM: Mouse
<220> FEATURE:
<221> NAME/KEY: DOMAIN
<222> LOCATION: (139)...(151)
<223> OTHER INFORMATION: proteolipid protein

<400> SEQUENCE: 4

His Ser Leu Gly Leu Trp Leu Gly His Pro Asp Lys Phe
 1               5                   10

<210> SEQ ID NO 5
<211> LENGTH: 13
<212> TYPE: PRT
<213> ORGANISM: Influenza virus
<220> FEATURE:
<221> NAME/KEY: DOMAIN
<222> LOCATION: (306)...(318)
<223> OTHER INFORMATION: hemagglutinin protein

<400> SEQUENCE: 5

-continued

```
Pro Lys Tyr Val Lys Gln Asn Thr Leu Lys Leu Ala Thr
1               5                   10
```

COPOLYMERS FOR SUPPRESSION OF AUTOIMMUNE DISEASES, AND METHODS OF USE

RELATED APPLICATIONS

This application is a divisional of and claims the benefit of U.S. patent application Ser. No. 12/005,239 filed in the U.S. Patent and Trademark Office Dec. 26, 2007, now U.S. Pat. No. 8,017,125 issued Sep. 13, 2011, and which is a divisional of and claims the benefit of U.S. patent application Ser. No. 10/406,783 filed in the U.S. Patent and Trademark Office Apr. 3, 2003, now U.S. Pat. No. 7,381,790 issued Jun. 3, 2008, and which is a continuation-in-part of PCT/US02/31399 filed Oct. 3, 2002 in the PCT Receiving Office of the U.S. Patent and Trademark Office, which claims priority from U.S. provisional application Ser. No. 60/326,705 filed Oct. 3, 2001 in the U.S. Patent and Trademark Office, each of which is hereby incorporated by reference in its entirety herein.

GOVERNMENT FUNDING

This invention was made in part with government support under grants CA47554 and AI49524 awarded by the National Institutes of Health. The government has certain rights in the invention.

TECHNICAL FIELD

The invention relates to design of copolymers having particular amino acids in specific molar ratios, synthesized into polypeptides of predetermined length and capable of suppression of symptoms and frequency of recurrent episodes of an autoimmune disease.

BACKGROUND

Multiple sclerosis (MS) is an inflammatory disease of the central nervous system affecting 0.1% of the population, and is associated in northern European caucasoid MS patients with the HLA-DR-2 (DRB1*1501) haplotype (Olerup, O. et al. 1991. *Tissue Antigens* 38:1-15). An animal model of MS, experimental autoimmune encephalomyelitis (EAE), is a T cell-mediated autoimmune disease. EAE can be induced by subcutaneous injection of peptides derived from myelin components such as myelin basic protein (MBP; Madsen, L. S. et al. 1999. *Nat. Genet.* 23:343-347), proteolipid protein (PLP; Greer, J. M. et al. 1992. *J. Immunol.* 149:783-788) or myelin oligodendrocyte glycoprotein (MOG; Mendel, I. et al. 1995. *Eur. J. Immunol.* 25:1951-1959).

In the course of EAE, autoreactive $CD4^+$ T cells recognize self-antigens presented by murine class II MHC molecules (e.g. $H\text{-}2A^s$), ultimately leading to pathological changes that can be monitored as clinical signs of disease. EAE provides a well studied system for testing the efficacy of potential therapeutic compounds to suppress the disease. These compounds have included cytokines (Leonard, J. P. et al. 1996. *Ann. N.Y. Acad. Sci.* 795:216-226), peptide antigens that induce anergy (Gaur, A. et al. 1992. *Science* 258:1491-1494) or that induce oral tolerance (Kennedy, K. J. et al. 1997. *J. Immunol.* 159: 1036-1044; Weiner, H. L. 1997. *Immunol. Today* 18:335-343), or altered peptide ligands (Pfeiffer, C. et al. 1995. *J. Exp. Med.* 181:1569-1574; Nicholson, L. B. et al. 1997. *Proc. Natl. Acad. Sci. USA* 94:9279-9284).

Copolymer 1 (Cop1; Copaxone®; YEAK) is a random amino acid copolymer of alanine (A), lysine (K), glutamic acid (E) and tyrosine (Y) in a molar ratio of approximately 5:3:1.5:1. Cop1 is synthesized in solution using N-carboxyamino acid anhydrides (Teitelbaum D. et al. 1971. *Eur. J. Immunol.* 1:242-248). Initially, this and other related copolymers were used to define the genetic basis of immune responsiveness, now known as class II MHC genes (McDevitt, H. O., and M. Sela. 1965. *J. Exp. Med.* 122:517-532; McDevitt, H. O., and M. Sela. 1967. *J. Exp. Med.* 126:969-978). Cop1, also known as poly (Y,E,A,K) or YEAK was found to be effective both in suppression of experimental allergic encephalomyelitis (Teitelbaum D. et al. 1971. *Eur. J. Immunol.* 1:242-248; Teitelbaum D. et al. 1973. *Eur. J. Immunol.* 3:273-279; Teitelbaum D, et al. 1974; *Clin. Immunol. Immunopathol* 3:256-262; Aharoni R. et al. 1993. *Eur. J. Immunol.* 23:17-25) and in the treatment of relapsing forms of multiple sclerosis (MS; Bornstein, M. B. et al. 1987. *N. Engl. J. Med.* 317:408-414; Johnson, K. P. et al. 1995. *Neurology* 45:1268-1276; Johnson, K. P. et al. 1998. *Neurology* 50:701-708).

Cop1 has been approved as a therapy for MS and currently is in wide use. However, while Cop1 reduces the MS relapse rate, it does not eliminate relapse, and is not curative for the disease. It is important to develop improved compositions and methods of use for treatment of MS, and for other autoimmune diseases.

SUMMARY

Certain aspects of the present invention relate to linear random amino acid copolymers made of amino acid residues $Xaa_1$, $Xaa_2$, Ala and Lys in a molar ratio which provides a copolymer having the desired biological properties recited herein. In certain preferred embodiments, the molar ration of $(Xaa_1+Xaa_2+K):A$ is in the range of 1:1 to 1:10. In certain preferred embodiments, the molar ration of K:A is in the range of 1:1.5 to 1:15. In certain preferred embodiments, the molar ration of $(Xaa_1+Xaa_2):(K+A)$ is in the range of 1:2 to 1:20. Expressions such as "$(Xaa_1+Xaa_2)$" means the sum of the molar ratios of $Xaa_1$ and $Xaa_2$, etc. $Xaa_1$ and $Xaa_2$ are, independently, residues having hydrophobic sidechains Exemplary naturally occurring amino acid residues include Ala, Gly, Ile, Leu, Met, Phe, Pro, Trp, Tyr, and Val. Non-naturally occurring amino acid analogs that can incorporated into the subject copolymers include residues having alkyl, alkenyl, cycloalkyl, heteroalkyl and aryl sidechains. In certain preferred embodiments, the hydrophobic sidechains have between 3 and 10 carbon atoms (in addition to the $C\alpha$ carbon), and may optionally include 1-3 heteroatoms such as O, S and N. Exemplary naturally occurring amino acid residues with this characteristic include Ile, Leu, Met, Phe, Trp, Tyr and Val. Preferably, $Xaa_1$ are $Xaa_2$ are different.

A feature of the invention is a linear random amino acid copolymer YFAK comprising tyrosine (Y), phenylalanine (F), alanine (A) and lysine (K). In a related embodiment, a molar ratio of (Y+F):A:K has a range of about 1:5:3 to about 1:10:3. The expression "(Y+F)" means the sum of the molar ratios of Y and F, compared to the molar ratios of each of A and K.

The amino acids are polymerized by a solid phase reaction; in an alternative embodiment, the amino acids are polymerized by solution chemistry. In a related embodiment, the molar ratio of F to Y is about 1, for example, the molar ratio of F to Y is at least about 2, or Y is about 4.

In an alternative embodiment, the molar ratio of Y is greater than F, for example, the molar ratio of Y to F is at least about 2, or the molar ratio of Y to F is at least about 4. In general, the copolymer is at least about 25 amino acid residues in length, for example, the copolymer is at least about 35 amino acid residues, at least about 50 amino acid residues, or at least about 70 amino acid residues in length.

In one embodiment, the invention provides a linear random amino acid copolymer comprising Y:F:A:K in a molar ratio having a range of about 0.2:0.8:5:3 to about 0.2:0.8:10:3. In a related embodiment, the invention provides a linear random amino acid copolymer comprising Y:F:A:K in a molar ratio having a range of about 0.5:0.5:5:3 to about 0.5:0.5:10:3. In another related embodiment, the invention provides a linear random amino acid copolymer comprising Y:F:A:K in a molar ratio having a range of about 0.8:0.2:5:3 to about 0.8:0.2:10:3. In general, the copolymer amino acids are polymerized using a solid phase reaction; alternatively, the copolymer amino acids are polymerized by solution phase chemistry.

In another aspect, the invention provides a linear random amino acid copolymer VFAK comprising valine (V), phenylalanine (F), alanine (A) and lysine (K). In another aspect, the invention provides a linear random amino acid copolymer VWAK comprising valine (V), tryptophan (W), alanine (A) and lysine (K). In another aspect, the invention provides a linear random amino acid copolymer VYAK comprising valine (V), tyrosine (Y), alanine (A) and lysine (K). In another aspect, the invention provides a linear random amino acid copolymer FAK comprising phenylalanine (F), alanine (A) and lysine (K), in a molar ratio F:A:K having a range of about 1:5:3 to about 1:10:3. In another aspect, the invention provides a linear random amino acid copolymer VAK comprising valine (V), alanine (A) and lysine (K) in a molar ratio V:A:K having a range of about 1:5:3 to about 1:10:3. In another aspect, the invention provides a linear random amino acid copolymer WAK comprising tryptophan (W), alanine (A) and lysine (K) in a molar ratio W:A:K having a range of about 1:5:3 to about 1:10:3. In another aspect, the invention provides a linear random amino acid copolymer VWAK comprising valine (V), tryptophan (W), alanine (A) and lysine (K), in a molar ratio (V+W):A:K having a range of about 1:5:3 to about 1:10:3. The expression "(V+W)" means the sum of the molar ratios of V and W, compared to the molar ratios of each of A and K.

In another aspect, the invention provides a linear random amino acid copolymer VWAK comprising valine (V), tryptophan (W), alanine (A) and lysine (K). In a related embodiment, a molar ratio V:W:A:K having a range of about 0.5:0.5:5:3 to about 0.5:0.5:10:3. In another aspect, the invention provides a linear random amino acid copolymer VEAK comprising valine (V), glutamic acid (E), alanine (A) and lysine (K). In a related embodiment, V:E:A:K has a molar ratio in the range of about 1:1.5:5:3 to about 1:1.5:10:3. In another aspect, the invention provides a linear random amino acid copolymer FEAK comprising phenylalanine (F), glutamic acid (E), alanine (A) and lysine (K). In a related embodiment, F:E:A:K has a molar ratio in the range of about 1:1.5:5:3 to about 1:1.5:10:3. In another aspect, the invention provides a linear random amino acid copolymer VYAK comprising valine (V), tyrosine (Y), alanine (A) and lysine (K). In a related embodiment, (V+Y):A:K has a molar ratio in the range of about 1:5:3 to about 1:10:3. The expression "(V+Y)" means the sum of the molar ratios of V and Y, compared to the molar ratios of each of A and K. In another aspect, the invention provides a linear random amino acid copolymer VYAK comprising valine (V), tyrosine (Y), alanine (A) and lysine (K). In a related embodiment, V:Y:A:K has a molar ratio of about 0.5:0.5:5:3 to about 0.5:0.5:10:3. Further, any of the compositions provided here may be provided in a pharmaceutically acceptable buffer, and/or in a unit dosage.

1. The featured copolymers herein are comprised of amino acids as described, and are further considered to be equivalent to copolymers sharing the amino acid compositions as described and also containing one or more additional substituents, for example, have one or more additional amino acids, such that the resulting copolymer has about the same function. For example, a copolymer FEAK, FAK, VWAK, VYAK, YFAK, or any of the copolymer compositions as provided herein, which is comprised substantially of this composition, i.e, is at least about 60%, or at least about 70%, or at least about 80%, or at least about 90%, or at least about 95% or about 99% the composition provided herein, and has about the same functional properties as a copolymer provided herein, is considered equivalent to the composition as provided herein. The function is considered to be about the same if a dosage of a composition herein that is effective for treating an autoimmune disease is about the same as a dosage of a copolymer comprising substantially the same substitutents as a composition herein, for treating the autoimmune disease. The copolymers herein can further comprise a modification which is at least one non-peptide bond. The non-peptide bond can be selected from the group consisting of: —$CH_2NH$—, —$CH_2S$—, —$CH_2CH_2$—, —$CH=CH$—, —$COCH_2$—, —$CH(OH)CH_2$—, and —$CH_2SO$—. For example, the non-peptide bond is —$CH_2NH$— or —$CH=CH$—.

The featured copolymer compositions herein can be combined with at least one additional therapeutic agent. In related embodiments, the additional therapeutic agent is an antibody, an enzyme inhibitor, an antibacterial, an antiviral, a steroid, a nonsteroidal anti-inflammatory, an antimetabolite, a cytokine, a cytokine blocking agent, an adhesion molecule blocking agent or a soluble cytokine receptor. For example, the cytokine is selected from the group consisting of β-interferon, interleukin-4 and interleukin-10.

An embodiment of the invention is a kit comprising at least one unit dosage of a copolymer described above.

2. A feature of the invention is a method of manufacture of a composition for use in treating a subject having an autoimmune disease, wherein the composition comprises any of random linear amino acid copolymers FAK, YFAK, VYAK, VWAK, VEAK and FEAK. In general, the copolymer has a length of at least about 50 residues, for example, at least about 70 residues. Further, in such a use, the composition further comprises a pharmaceutically acceptable carrier. Further, the use can involve administering the composition in an effective dose. An "effective dose" is an amount of the composition that remediates either or both of clinical symptoms and frequency of recurrence of an autoimmune disease. Prior to administering, the copolymer is selected for inhibiting binding of an autoantigenic peptide to an MHC class II protein associated with the autoimmune disease. For example, the copolymer that inhibits a class II-specific T cell response to an MHC class II protein-peptide complex is selected. The autoimmune disease is selected from the group consisting of Hashimoto's thyroiditis; idiopathic myxedema, a severe hypothyroidism; multiple sclerosis, a demyelinating disease; myasthenia gravis; Guillain-Barre syndrome; systemic lupus erythematosis; uveitis; autoimmune oophoritis; chronic immune thrombocytopenic purpura; colitis; diabetes; Grave's disease; psoriasis; pemphigus vulgaris; and rheumatoid arthritis, and others. In a preferred embodiment, the autoimmune disease is multiple sclerosis; the autoimmune disease is rheumatoid arthritis; or the autoimmune disease is diabetes. An additional therapeutic agent, can be co-administered, for example, the additional therapeutic agent is an antibody, an enzyme inhibitor, an antibacterial agent, an antiviral agent, a steroid, a nonsteroidal anti-inflammatory agent, an antimetabolite, a cytokine, a cytokine blocking agent, an adhesion molecule blocking agent, or a soluble cytokine receptor. The cytokine is: interferon-β, interleukin-4, or interleukin-10. The enzyme inhibitor is a protease inhibitor or a cyclooxygenase inhibitor. The copolymers used in the methods herein can further comprise a modification which is at least one non-peptide bond. The non-peptide bond can be selected from the group consisting of: —CH$_2$NH—, —CH$_2$S—, —CH$_2$CH$_2$—, —CH═CH—, —COCH$_2$—, —CH(OH)CH$_2$—, and —CH$_2$SO—. For example, the non-peptide bond is —CH$_2$NH— or —CH═CH—.

BRIEF DESCRIPTION OF THE DRAWINGS

FIG. 6 is a set of graphs showing suppression by different random copolymers FAK, YFAK 0.2:0.8, YFAK 0.8:0.2, YFAK 0.5:0.5, or Copaxone® of EAE induced with PLP 139-151 (SEQ ID NO: 4) peptide. SJL/J mice were co-injected subcutaneously with 50 μg of PLP 139-151 (SEQ ID NO: 4) peptide and 500 μg of the indicated random copolymers, or immunized with PLP 139-151 (SEQ ID NO: 4) alone. Progression of the disease was monitored for the appearance of clinical symptoms for the days after disease induction shown on the abscissa. FIG. 6A shows the results of the mean daily score of clinical symptoms as shown on the ordinate for each group of five to nine mice per group in each of two experiments.

DESCRIPTION OF SPECIFIC EMBODIMENTS

Figure 1B:
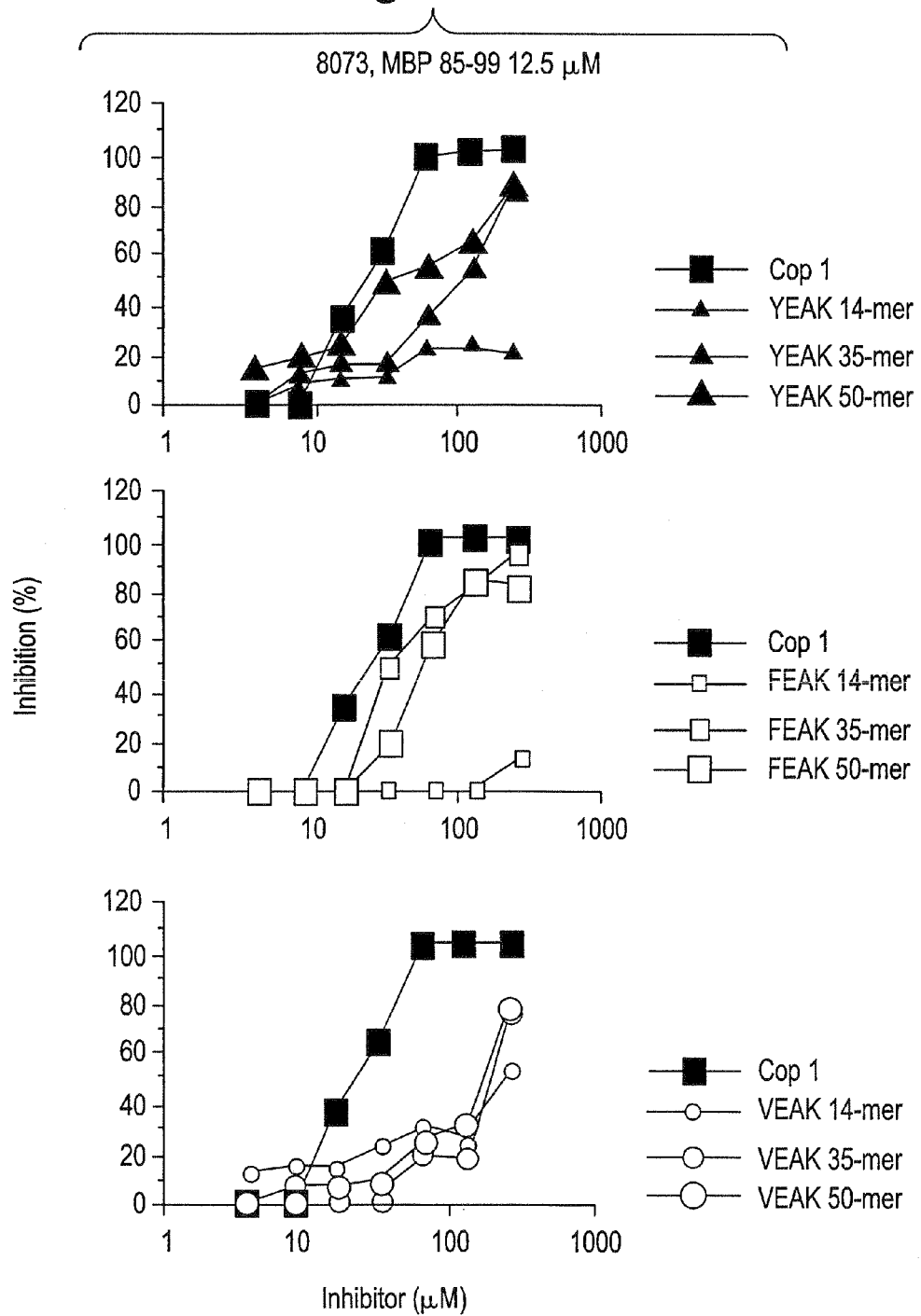
FIG. 1 is a set of panels of graphs showing inhibition of HLA-DR-2-restricted MBP 84-102-specific T cell lines 2E12 (FIG. 1A), 8073 (FIG. 1B) and Hy1B (FIG. 1C), in the presence of the random copolymers. Irradiated L466 (FIG. 1A) or MGAR (FIGS. 1B, 1C) cells were co-incubated in duplicate with MBP 85-99 (SEQ ID NO: 2) at a final concentration of 4 μM (A) or 12.5 μM (FIGS. 1B, 1C) and different concentrations of each of the random copolymers as indicated for 2 hr at 37° C., then T cells were added and incubated for 24 hr at 37° C. Supernatants (30 μl) were incubated with IL-2-dependent cytolytic T-cell lymphocytes (CTLL), followed by labeling with $^3$H-thymidine (1 μCi/well) for 12 hr.

Unless the context otherwise requires, as used in this description and in the following claims, the terms below shall have the meanings as set forth:

The term "autoimmune condition" or "autoimmune disease" means a disease state caused by an inappropriate immune response that is directed to a self-encoded entity which is known as an autoantigen. The copolymer compounds provided herein can be used to treat symptoms of an autoimmune disease, a class of disorder which includes Hashimoto's thyroiditis; idiopathic myxedema, a severe hypothyroidism; multiple sclerosis, a demyelinating disease marked by patches or hardened tissue in the brain or the spinal cord; myasthenia gravis which is a disease having progressive weakness of muscles caused by autoimmune attack on acetylcholine receptors at neuromuscular junctions; Guillain-Barre syndrome, a polyneuritis; systemic lupus erythematosis; uveitis; autoimmune oophoritis; chronic immune thrombocytopenic purpura; colitis; diabetes; Grave's disease, which is a form of hypothyroidism; psoriasis; pemphigus vulgaris; and rheumatoid arthritis (RA).

The term "demyelinating condition" includes a disease state in which a portion of the myelin sheath, consisting of plasma membrane wrapped around the elongated portion of the nerve cell, is removed by degradation. A demyelinating condition can arise post-vaccination, post-anti TNF treatment, post-viral infection, and in MS.

The term "derivative" of an amino acid means a chemically related form of that amino acid having an additional substituent, for example, N-carboxyanhydride group, a γ-benzyl group, an ε,N-trifluoroacetyl group, or a halide group attached to an atom of the amino acid.

The term "analog" means a chemically related form of that amino acid having a different configuration, for example, an isomer, or a D-configuration rather than an L-configuration, or an organic molecule with the approximate size, charge, and shape of the amino acid, or an amino acid with modification to the atoms that are involved in the peptide bond, so that the copolymer having the analog residue is more protease resistant than an otherwise similar copolymer lacking such analog, whether the analog is interior or is located at a terminus of the copolymer, compared to the copolymer without the analog.

The phrases "amino acid" and "amino acid copolymer" can include one or more components which are amino acid derivatives and/or amino acid analogs as defined herein, the derivative or analog comprising part or the entirety of the residues for any one or more of the 20 naturally occurring amino acids indicated by that composition. For example, in an amino acid copolymer composition having one or more tyrosine residues, a portion of one or more of those residues can be substituted with homotyrosine. Further, an amino acid copolymer having one or more non-peptide or peptidomimetic bonds between two adjacent residues, is included within this definition.

The term "hydrophobic" amino acid means aliphatic amino acids alanine (A, or ala), glycine (G, or gly), isoleucine (I, or ile), leucine (L, or leu), methionine (M, or met), proline (P, or pro), and valine (V, or val), the terms in parentheses being the one letter and three letter standard code abbreviations for each amino acid, and aromatic amino acids tryptophan (W, or trp), phenylalanine (F, or phe), and tyrosine (Y, or tyr). These amino acids confer hydrophobicity as a function of the length of aliphatic and size of aromatic side chains, when found as residues within a copolymer or other polypeptide.

The term "charged" amino acid means amino acids aspartic acid (D or asp), glutamic acid (E or glu), arginine (R or arg) and lysine (K or lys), which confer a positive (lys, and arg) or negative (asp, glu) charge at physiological values of pH on an aqueous solution of a copolymer or other amino acid composition containing one or more residues of these amino acids. Histidine (H or his) is hydrophobic at pH 7, and charged at pH 6.

The term "anergy" means unresponsiveness of the immune system of a subject to an antigen.

The term "subject" as used herein indicates a mammal, including a human.

The term "heterologous cell" means a cell for production of an MHC protein which is unrelated to a cell of a subject, e.g., the heterologous cell is not a cell of a mammal. The heterologous cell for example can be from a cold blooded animal, for example, from an invertebrate; the heterologous cell is an insect cell, or a cell of a microorganism such as a yeast cell.

The term "surfaces of Class II MHC HLA-DR-2 protein" includes the portions of the protein molecule in its three-dimensional configuration which are in contact with its external environment, including those features of the protein that interact with aqueous solvent and are capable of binding to other cell components such as nucleic acids, other proteins, and peptides.

The terms "P1 pocket" and "P4 pocket" include three dimensional polymorphic regions on the peptide binding surface of the Class II MHC protein molecule that accommodate amino acid residue side chains from a peptide that is bound to the Class II MHC protein (Fridkis-Hareli, M. et al. 1998. *J. Immunol.* 160:4386-4397; Fridkis-Hareli, M. et. al. 2000. *Human Immunol.* 61:640; Fridkis-Hareli, M. et al. 2001. *Human Immunol.* 62:753-763), including a bound naturally occurring antigen or epitope, and a bound synthetic peptide or copolymer.

The terms "P-1 position" and "P5 position" refer to amino acid residues on the Class II MHC protein molecule peptide complex which directly contact the T-cell receptor (Fridkis-Hareli, M. et. al. 2000. *Human Immunol.* 61:640; Fridkis-Hareli, M. et al. 2001. *Human Immunol.* 62:753-763). The P-1 position refers to the amino acid which precedes the amino acid residue of the peptide that occupies the P1 pocket. The P5 position refers to the amino acid residue that follows the amino acid residue that occupies the P4 pocket.

The term "antigen binding groove" refers to a three dimensional antigen interactive site on the surface of the Class II MHC protein molecule (Stern, L. J. et. al., *Nature* 368:215 (1994)) that is formed by surfaces of both the α and β subunits of the Class II MHC protein molecule.

The term "pharmaceutically acceptable carrier" includes any and all solvents, dispersion media, coatings, antimicrobials such as antibacterial and antifungal agents, isotonic and absorption delaying agents and the like that are physiologically compatible. Preferably, the carrier is suitable for intravenous, intramuscular, oral, intraperitoneal, transdermal, or subcutaneous administration, and the active compound can be coated in a material to protect it from inactivation by the action of acids or other adverse natural conditions.

An autoimmune disease results when a host's immune response fails to distinguish foreign antigens from self molecules (autoantigens) thereby eliciting an aberrant immune response. The immune response towards self molecules in an autoimmune disease results in a deviation from the normal state of self-tolerance, which involves the destruction of T cells and B cells capable of reacting against autoantigens, which has been prevented by events that occur in the development of the immune system early in life. The cell surface proteins that play a central role in regulation of immune responses through their ability to bind and present processed peptides to T cells are the major histocompatibility complex (MHC) molecules (Rothbard, J. B. et al., *Annu. Rev. Immunol.* 9:527 (1991)).

In addition to MS, other demyelinating conditions have been found to occur, for example, post-viral infection, post-vaccination, post-encephalomyelitis (Wucherpfennig K. W. et al. 1991. *Immunol. Today* 12:277-282) and following administration of certain anti-TNF agents.

Copolymers of Amino Acids as Therapeutic Agents for Autoimmune Diseases

Methods of the invention include use of a class of agents that can bind to Class II MHC proteins encoded by particular alleles. Such an agent can bind to a particular Class II MHC protein, and thus inhibit and/or prevent the binding of an autoantigen involved in an autoimmune disease, or upon binding can induce anergy, so that there is no response of the immune system to the autoantigen.

A number of therapeutic agents have been developed to treat autoimmune diseases. For example, agents have been developed that can, by inhibiting a cyclooxygenase, prevent formation of low molecular weight inflammatory compounds. Also, agents are available that can function by inhibiting a protein mediator of inflammation, by sequestering the inflammatory protein tumor necrosis factor (TNF) with an anti-TNF specific monoclonal antibody fragment, or with a soluble form of the TNF receptor. Finally, agents are available that target and inhibit the function of a protein on the surface of a T cell (the CD4 receptor or the cell adhesion receptor ICAM-1) thereby preventing a productive interaction with an antigen presenting cell (APC). However, compositions which are natural folded proteins as therapeutic agents can incur problems in production, formulation, storage, and delivery. Further, natural proteins can be contaminated with pathogenic agents such as viruses and prions.

An additional target for inhibition of an autoimmune response is the set of lymphocyte surface proteins represented by the MHC molecules. Specifically, these proteins are encoded by the Class II MHC genes designated as HLA (human leukocyte antigen)-DR, -DQ and -DP. Each of the MHC genes is found in a large number of alternative or allelic forms within a mammalian population. The genomes of subjects affected with certain autoimmune diseases, for example, MS and rheumatoid arthritis (RA), are more likely to carry one or more characteristic Class II MHC alleles, to which that disease is linked.

A potential source of agents for treatment of MS and other demyelinating conditions is to identify peptides that bind selectively in vitro to a purified Class II MHC allele protein molecule, particularly to a protein which is a product of an Class II MHC allele associated with demyelinating conditions. In addition, the agent should bind to that protein as it occurs on the surfaces of antigen presenting cells in vivo, and thereby block, anergize, or inactivate the class of T cells that are responsible for the demyelinating condition, such as MS.

The Class II MHC protein consists of two approximately equal-sized subunits, α and β, which are transmembrane proteins. A peptide-binding cleft, which is formed by protein features of both α and β subunits, is the site of presentation of the antigen to T cells. There are at least three types of Class II MHC molecules: HLA-DR, -DQ, and -DP, and there are numerous alleles of each type. The Class II MHC molecules are expressed predominantly on the surfaces of B lymphocytes and antigen presenting cells such as macrophages and dendritic cells (Mengle-Gaw, L., *The Major Histocompatibility Complex* (MHC), in the Encyclopedia of Molecular Biology, Oxford: Blackwell Science Ltd., 1994, pp. 602-606).

An embodiment of the invention includes a novel method for treating autoimmune diseases, by targeting Class II MHC molecules with a class of compounds identified as copolymers that include three or more different amino acids.

A copolymer of the invention can be synthesized using fmoc- or tBoc-protected initiating amino acid analogs, or the like, which are immobilized on a resin in an automated peptide synthesis apparatus for further polymerization (solid state synthesis). The amino acids are polymerized in molar ratios that can be adjusted to provide a copolymer with optimal binding characteristics.

Synthesis procedures can include providing a solution which is a mixture of the chosen amino acids in an activated form, for example, activated as an N-carboxy anhydride, in the appropriate molar ratios of each of the appropriately derivatized amino acid precursors (derivatized to protect certain functional groups, such as the ε amino group of L-lysine, for example the precursor ε,N-trifluoroacetyl-L-lysine). Alternatively, the synthesis procedure can involve online mixing during the synthetic procedure of derivatized precursors of the selected amino acids in the preferred molar ratios. Heteropolymer synthesis services can be obtained commercially, for example, at Chiron Technologies, Clayton, Australia, the Harvard Medical School Biopolymer Laboratory, Boston, Mass., and at Advanced ChemTech, Inc., Louisville, Ky.

Examples of such resin supports for peptide synthesis include a Merrifield resin, chloromethylated polystyrene with 1% DVB cross-links; an fmoc amino acid Wang resin, 4-benzyloxybenzyl alcohol, the resins being pre-loaded with an amino acid (for example, fmoc-D-trp(boc)-Wang resin). Resins are available in different mesh sizes, for example 100-200 mesh, and high loading or low loading densities of functionalization of the initiating amino acid.

A solution of the different derivatized amino acids to be polymerized into the composition of the invention, preferably protected as is conventional in peptide synthesis, is added to sample of beads e.g., fmoc. Reagents for synthesis, for deblocking, and for cleavage of the complete copolymer molecules for removal from the resin are available from manufacturers of the apparatus (Applied Biosystems Peptide Synthesizer, Foster City, Calif., or Advanced ChemTech, Louisville, Ky.); see e.g., M. Bodansky, *Principles of Peptide Synthesis*, 2nd Ed., Springer-Verlag, 1991, the contents of which are herein incorporated by reference. Additional amino acids or analogs or derivatives of amino acids, can be added to the at least three amino acids selected to comprise the copolymers, to substitute for a small proportion of those amino acids, to provide, for example, a copolymer having increased protease resistance and therefore having enhanced pharmacological properties such as longer in vivo lifetime. Examples of analogs are homotyrosine, or other substituted tyrosine derivatives, and aminobutyric acid, each available as an fmoc derivative from Advanced ChemTech.

The invention in other embodiments provides copolymers having non-peptide bonds between one or more of the amino acid residues in the copolymer backbone. The presence of non-peptide bonds can confer, inter alia, improved pharmacological properties on the copolymer analogs including improved binding to Class II MHC protein, increased serum half-life, and/or improved bioavailability. Such copolymer peptidomimetics can be synthesized having the same molar ratios of amino acid precursors as a "parent" copolymer, i.e., the parent copolymer having peptide bonds and comprising amino acids in random sequence, however using an amino acid analog that forms a bond that is not a peptide bond. The copolymer analogs are potential therapeutic agents for autoimmune diseases, as they retain the ability of to parent copolymer to inhibit or to prevent interaction of an auto-antigenic peptide, e.g., an auto-antigen associated with MS such as MBP 58-99 (SEQ ID No: 2), to interact with a Class II MHC protein, for example, with Class II MHC DR-2 protein, and to prevent or cure the autoimmune disease such as EAE in mice or MS in humans.

For illustrative purposes, peptidomimetics of the present invention can be generated using, for example, benzodiazepines (e.g., see Freidinger et al. in *Peptides: Chemistry and Biology*, G. R. Marshall ed., ESCOM Publisher: Leiden, Netherlands, 1988), substituted gama lactam rings (Garvey et al. in *Peptides: Chemistry and Biology*, G. R. Marshall ed., ESCOM Publisher: Leiden, Netherlands, 1988, p123), C-7 mimics (Huffman et al. in *Peptides: Chemistry and Biology*, G. R. Marshall ed., ESCOM Publisher: Leiden, Netherlands, 1988, p. 105), keto-methylene pseudopeptides (Ewenson et al. (1986) *J Med Chem* 29:295; and Ewenson et al. in *Peptides: Structure and Function* (Proceedings of the 9th American Peptide Symposium) Pierce Chemical Co. Rockland, Ill., 1985), β-turn dipeptide cores (Nagai et al. (1985) *Tetrahedron Lett* 26:647; and Sato et al. (1986) *J Chem Soc Perkin Trans* 1:1231), β-aminoalcohols (Gordon et al. (1985) *Biochem Biophys Res Commun* 126:419; and Dann et al. (1986) *Biochem Biophys Res Commun* 134:71), diaminoketones (Natarajan et al. (1984) *Biochem Biophys Res Commun* 124:141), and methyleneamino-modified (Roark et al. in *Peptides: Chemistry and Biology*, G. R. Marshall ed., ESCOM Publisher: Leiden, Netherlands, 1988, p 134). Also, see generally, Session III: Analytic and synthetic methods, in *Peptides: Chemistry and Biology*, G. R. Marshall ed., ESCOM Publisher: Leiden, Netherlands, 1988).

In addition, the present invention specifically contemplates the use of conformationally restrained mimics of peptide secondary structure. Numerous surrogates have been developed for the amide bond of peptides. Frequently exploited surrogates for the amide bond include the following groups (i) trans-olefins, (ii) fluoroalkene, (iii) methyleneamino, (iv) phosphonamides, and (v) sulfonamides.

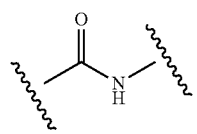

amine bond

Examples of Surrogates

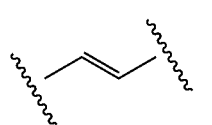

trans olefin

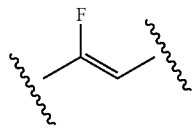

fluoroalkene

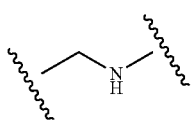

methyleneamino

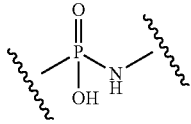

phosphonamide

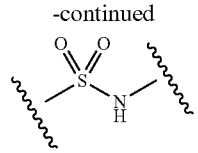

sulfonamide

Additionally, peptidomimietics based on more substantial modifications of the backbone of the copolymer can be used. Peptidomimetics which fall in this category include (i) retro-inverso analogs, and (ii) N-alkyl glycine analogs (so-called peptoids).

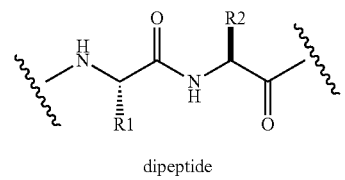

dipeptide

Examples of Analogs

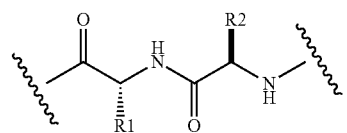

retro-inverso

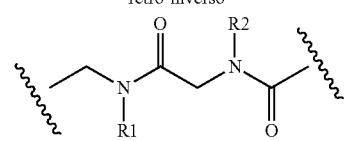

N-alkyl glycine

Furthermore, the methods of combinatorial chemistry are being brought to bear on the development of new peptidomimetics. For example, one embodiment of a so-called "peptide morphing" strategy focuses on the random generation of a library of peptide analogs that comprise a wide range of peptide bond substitutes. See, for example, PCT Publication WO9948897; Gierasch et al. (2000) *Org. Lett.* 2:3999-4002; Michielin et al. (2002) *J. Am. Chem. Soc.* 124: 11131-11141; and Harrison et al. (2002) *J. Am. Chem. Soc.* 124:13352-13353.

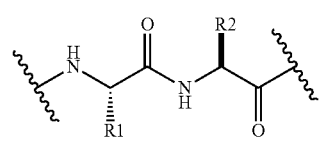

dipeptide

↓ peptide morphing

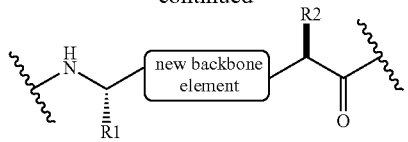

In an exemplary embodiment, the copolymer can be derived as a retro-inverso peptidomimetic. Retro-inverso peptidomimetics can be made according to the methods known in the art, such as that described by the Sisto et al. U.S. Pat. No. 4,522,752. As a general guide, cites which are most susceptible to proteolysis are typically altered, with less susceptible amide linkages being optional for mimetic switching The final product, or intermediates thereof, can be purified by HPLC.

In another illustrative embodiment, the copolymer can be derived as a retro-enatio peptidomimetic. Retro-enantio analogs such as this can be synthesized commercially available D-amino acids (or analogs thereof) and standard solid- or solution-phase peptide-synthesis techniques.

In still another illustrative embodiment, trans-olefin derivatives can be made for any of the subject copolymers. A trans-olefin peptidomimetic can be synthesized according to the method of Y. K. Shue et al. (1987) *Tetrahedron Letters* 28:3225 and also according to other methods known in the art. It will be appreciated that variations in the cited procedure, or other procedures available, may be necessary according to the nature of the reagent used.

Still another class of peptidomimetic derivatives include phosphonate derivatives. The synthesis of such phosphonate derivatives can be adapted from known synthesis schemes. See, for example, Loots et al. in *Peptides: Chemistry and Biology*, (Escom Science Publishers, Leiden, 1988, p. 118); Petrillo et al. in *Peptides: Structure and Function* (Proceedings of the 9th American Peptide Symposium, Pierce Chemical Co. Rockland, Ill., 1985).

Many other peptidomimetic structures are known in the art and can be readily adapted for use in the subject copolymers. To illustrate, the copolymer may incorporate the 1-azabicyclo [4.3.0]nonane surrogate (see Kim et al. (1997) *J. Org. Chem.* 62:2847), or an N-acyl piperazic acid (see Xi et al. (1998) *J. Am. Chem. Soc.* 120:80), or a 2-substituted piperazine moiety as a constrained amino acid analog (see Williams et al. (1996) *J. Med. Chem.* 39:1345-1348). In still other embodiments, certain amino acid residues can be replaced with aryl and bi-aryl moieties, e.g., monocyclic or bicyclic aromatic or heteroaromatic nucleus, or a biaromatic, aromatic-heteroaromatic, or biheteroaromatic nucleus.

Advantages of the copolymer peptidomimetics, in comparison to the copolymers having only peptide bonds, can include: more economical production, greater chemical stability, enhanced pharmacological properties (half-life, absorption, potency, efficacy, etc.), altered specificity (e.g., a broader or a narrower spectrum of biological activities), and reduced antigenicity. Without being limited by any particular theory or mechanism, it is envisioned that a non-peptide bond located at one or both of the copolymer termini reduces or eliminates degradation of the copolymer analog by circulating processive exopeptidases, and prolongs the half-life of the copolymer following administration to a subject.

Therapeutic Compositions in the Methods of the Invention

A pharmaceutically acceptable carrier includes any and all solvents, dispersion media, coatings, antimicrobials such as antibacterial and antifungal agents, isotonic and absorption delaying agents and the like that are physiologically compatible. Preferably, the carrier is suitable for intravenous, intramuscular, oral, intraperitoneal, transdermal, or subcutaneous administration, and the active compound can be coated in a material to protect it from inactivation by the action of acids or other adverse natural conditions.

The methods of the invention include incorporation of a copolymer into a pharmaceutical composition suitable for administration to a subject. A composition of the present invention can be administered by a variety of methods known in the art as will be appreciated by the skilled artisan. The active compound can be prepared with carriers that will protect it against rapid release, such as a controlled release formulation, including implants, transdermal patches, and microencapsulated delivery systems. Many methods for the preparation of such formulations are patented and are generally known to those skilled in the art. See, e.g., *Sustained and Controlled Release Drug Delivery Systems*, J. R. Robinson, Ed., Marcel Dekker, Inc., NY, 1978. Therapeutic compositions for delivery in a pharmaceutically acceptable carrier are sterile, and are preferably stable under the conditions of manufacture and storage. The composition can be formulated as a solution, microemulsion, liposome, or other ordered structure suitable to high drug concentration.

Dosage regimens can be adjusted to provide the optimum desired response (e.g., a therapeutic response). For example, a single bolus can be administered, several divided doses can be administered over time, or the dose can be proportionally reduced or increased as indicated by the exigencies of the disease situation.

In general, an embodiment of the invention is to administer a suitable daily dose of a therapeutic copolymer composition that will be the lowest effective dose to produce a therapeutic effect, for example, mitigation of symptoms. The therapeutic heteropolymer compounds of the invention are preferably administered at a dose per subject per day of at least about 2 mg, at least about 5 mg, at least about 10 mg or at least about 20 mg as appropriate minimal starting dosages. In general, the compound of the effective dose of the composition of the invention can be administered in the range of about 50 to about 400 micrograms of the compound per kilogram of the subject per day.

A physician or veterinarian having ordinary skill in the art can readily determine and prescribe the effective dose of the pharmaceutical composition required. For example, the physician or veterinarian could start doses of the compound of the invention employed in the pharmaceutical composition at a level lower than that required in order to achieve the desired therapeutic effect, and increase the dosage with time until the desired effect is achieved.

In another embodiment, the pharmaceutical composition includes also an additional therapeutic agent. Thus in a method of the invention the pharmaceutical copolymer composition can be administered as part of a combination therapy, i.e. in combination with an additional agent or agents. Examples of materials that can be used as combination therapeutics with the copolymers for treatment of autoimmune disease and arthritic conditions as additional therapeutic agents include: an antibody or an antibody fragment that can bind specifically to an inflammatory molecule or an unwanted cytokine such as interleukin-6, interleukin-8, granulocyte macrophage colony stimulating factor, and tumor necrosis factor-α; an enzyme inhibitor which can be a protein, such as $\alpha_1$-antitrypsin, or aprotinin; an enzyme inhibitor which can be a cyclooxygenase inhibitor; an engineered binding protein, for example, an engineered protein that is a protease inhibitor such an engineered inhibitor of a kallikrein; an antibacterial agent, which can be an antibiotic such as amoxicillin, rifampicin, erythromycin; an antiviral agent, which can be a low molecular weight chemical, such as acyclovir; a steroid, for example a corticosteroid, or a sex steroid such as progesterone; a non-steroidal anti-inflammatory agent such as aspirin, ibuprofen, or acetaminophen; an anti-cancer agent such as methotrexate, cis-platin, 5-fluorouracil, or adriamycin; a cytokine blocking agent; an adhesion molecule blocking agent; or a cytokine.

An additional therapeutic agent can be a cytokine, which as used herein includes without limitation agents which are naturally occurring proteins or variants and which function as growth factors, lymphokines, interferons particularly interferon-β, tumor necrosis factors, angiogenic or antiangiogenic factors, erythropoietins, thrombopoietins, interleukins, maturation factors, chemotactic proteins, or the like. An additional agent to be added to a copolymer of amino acids which are embodiments of the invention herein can be a different copolymer, for example, Copaxone® which is a YEAK or Cop 1, or a copolymer comprising a subset of these or other amino acids (Aharoni et al. WO 00/05250, PCT/US99/16747), or an oligopeptide or peptide derivative (Strominger et al. WO 00/05249, PCT/US99/16617; WO 02/59143, PCT/US02/02071). Preferred therapeutic agents to be used in combination with a composition of the invention and which are cytokines include interferon-β, interleukin-4 and interleukin-10.

A therapeutic agent to be used with the composition of the invention can be an engineered binding protein, known to one of skill in the art of remodeling a protein that is covalently attached to a virion coat protein by virtue of genetic fusion (Ladner, R. et al., U.S. Pat. No. 5,233,409; Ladner, R. et al., U.S. Pat. No. 5,403,484), and can be made according to methods known in the art. A protein that binds any of a variety of other targets can be engineered and used in the present invention as a therapeutic agent in combination with a heteropolymer of the invention.

An improvement in the symptoms as a result of such administration is noted by a decrease in frequency of recurrences of episodes of MS, by decrease in severity of symptoms, and by elimination of recurrent episodes for a period of time after the start of administration. A therapeutically effective dosage preferably reduces symptoms and frequency of recurrences by at least about 20%, for example, by at least about 40%, by at least about 60%, and by at least about 80%, or by about 100% elimination of one or more symptoms, or elimination of recurrences of the autoimmune disease, relative to untreated subjects. The period of time can be at least about one month, at least about six months, or at least about one year.

Methods of use of random synthetic copolymers can be the basis of treating other autoimmune diseases which are associated with HLA-DR gene products, by competing with candidate autoantigens for binding to these protein receptor molecules, or by inducing T cell anergy or even T cell apoptosis, or by suppression of T cells, such that subsequent T cell response to an autoantigen is inhibited in vivo. Further, synthetic copolymers having one or more additional components, such as amino acid analogs or derivatives added in varying quantities into the polymerization reaction, can be effective inhibitors of a variety of autoimmune T cell responses.

The activity of Cop1 appears to involve, as a first step, binding to the surface of antigen-presenting cells (APC), for example to class II MHC proteins (Fridkis-Hareli M. et al. 1994. Proc. Natl. Acad. Sci. USA 91:4872-4876), following which its effectiveness may be due either to competition with myelin antigens (for example, MBP, PLP, MOG) for activation of specific effector T cells recognizing peptide epitopes derived from these proteins (Ben-Nun, A. et al. 1996. J. Neurol. 243:S14-22; Teitelbaum, D. et al. 1996. J. Neuroimmunol. 64:209-217), and/or induction of antigen-specific regulatory T cells (Aharoni R. et al. 1993. Eur. J. Immunol. 23:17-25).

Examination of additional copolymers and investigation of the mechanisms involved in their activities could potentially result in information that could lead to improved therapeutic reagents. Recent studies have shown that virtually all of the large variety of copolymers found in the random mixture of YEAK bound to purified molecules of each of human HLA-DR1, -DR-2 and -DR4 molecules, showing that YEAK generally binds to purified class II MHC proteins (Fridkis-Hareli, M., and J. L. Strominger. 1998. J. Immunol. 160:4386-4397). Cop1 further competes for binding of MBP 85-99 to HLA-DR-2 (DRB1*1501) and inhibits responses of DR-2-restricted T cells to MBP 85-99. Study of the binding to class II MHC molecules of random copolymers containing only 3 of the 4 amino acids of Cop1, for example, YAK, revealed that YAK is the most effective (Fridkis-Hareli, M. et al. 1999. Int. Immunol. 11:635-641).

The binding motif of Cop1 to the MS-associated molecule HLA DR-2 (DRB1*1501) shows E at P-2, K at P-1 and Y at P1, with no preferences observed at other positions (Fridkis-Hareli, M. et al. 1999. J. Immunol. 162:4697-4704). Further, A is overrepresented at P1. As P1 is the anchor position, binding of Y at this position was not anticipated. The P1 pocket in proteins encoded by the DR-2 allele is small (due to the presence of β86Val rather than β86Gly), and overrepresentation of A at this position may result from this fact. The effect of K at P-1 appears to be due to stabilization of binding by the interaction of K with residues in the top of the α1 helix, similarly to residue K at P-1 of HA 306-318 (SEQ ID NO:5) complexed with HLA-DR1 which can interact with the side chains of α1 helix residues at Sα53 or Eα55 (Stern, L. J. et al. 1994. Nature 368:215-221).

Copolymers designed according to the binding motif of MBP 85-99 (Wucherpfennig, K. W. et al. 1994. J. Exp. Med. 179:279-290) might be better therapeutic agents than Cop1. As provided herein, several random three- and four-amino acid copolymers, each synthesized as 14-, 35- and 50-mers in length, were made by the solid phase method. Design of these copolymers was made primarily by choice of amino acids with reference to the anchor residues of MBP 85-99 bound to HLA-DR-2 (DRB1*1501) (Wucherpfennig, K. W. et al. 1994. J. Exp. Med. 179:279-290; Smith, K. J. et al. 1998. J. Exp. Med. 19:1511-1520), particularly the P1 anchor, to improve the effectiveness of the copolymers. Effects of these copolymers on autoantigen-specific T cell responses in MS, and on disease progression of EAE, an animal model of MS, are shown in the Examples below.

A major goal in the treatment of autoimmune diseases has been development of antigen-specific immunomodulating therapies that interfere with the trimolecular interaction of the autoreactive T cell receptor (TCR) with the autoantigenic peptides presented by self MHC receptors at the surface of antigen-presenting cells. These immunotherapies of T cell-mediated autoimmune diseases have been successful in animal models with known target antigens (see, for example, Weiner, H. L. 1997. Immunol. Today 18:335-343; Nicholson, L. B. et al. 1997. Proc. Natl. Acad. Sci. USA 94:9279-9284). The use of altered peptide ligands (APL) has been used both to treat EAE (Nicholson, L. B. et al. 1997. Proc. Natl. Acad. Sci. USA 94:9279-9284; Brocke, S. et al. 1996. Nature 379:343-346) and recently to treat MS (Bielekova, B. et al. 2000.

Nat. Med. 10:1167-1175; Kappos, L. et al. 2000. Nat. Med. 10:1176-1182), with contradictory findings.

Cop1 (Copaxone®), an approved therapy for relapsing-remitting MS, was proposed to act as a promiscuous binder to class II MHC molecules (Fridkis-Hareli, M., and J. L. Strominger. 1998. J. Immunol. 160:4386-4397), as an antagonist of the TCR (Aharoni, R. et al., 1999. Proc. Natl. Acad. Sci. USA 96: 634-639), and/or as an inducer of suppressor cells (Aharoni R. et al. 1993. Eur. J. Immunol. 23:17-25). Copaxone® is currently in wide use, has shown little or no toxicity, and has sustained efficacy in MS patients over a period of 6 years (Johnson, K. P. et al. 2000. Mult. Scler. 6:255-266). However, this agent was found to reduce frequency of relapse by about 30%, but did not eliminate relapse. Development of novel compounds may provide improved therapeutic agents for MS and possibly for other autoimmune disorders.

In Examples 1-6, an optimal size of copolymers described herein was determined using copolymers which are 14-, 35- or 50-mers in length. Since the 50-mers are shown herein to be most efficient in binding HLA-DR-2 and in inhibiting MBP-specific T cell responses, the additional copolymers used in Examples 7-11 were all synthesized as 50-mers. A size of 50 amino acids or longer, found here to provide efficient inhibition of antigen presentation and suppression of EAE, suggests that the random copolymers herein act by binding to and then clustering class II MHC molecules in one portion of the cell membrane, similarly to Copaxone® (Fridkis-Hareli, M. et al. 1997 Int. Immunol. 9: 925-34) or oligomerized T cell epitopes (Rotzschke, O. et al. 1997 Proc. Natl. Acad. Sci. USA 94: 14642-14647).

The residues in the random copolymers in Examples 7-11 herein were designed mainly on the basis of the anchor residues of the immunodominant T cell epitope MBP 85-99 peptide (SEQ ID NO: 2). The Y in Copolymer 1 was found in the presumed P1 pocket of the HLA DR-2 (DRB1*1501) molecule (Fridkis-Hareli, M. et al. 1999 J. Immunol. 162: 4697-4704), although Y may be too large for this pocket which has a good fit with F, and accommodates V89 in MBP85-99. Moreover, the F92 in MBP 85-99 (SEQ ID NO: 2) is in the P4 pocket (Smith, K. J. et al. 1998 J. Exp. Med. 19: 1511-1520), but Y or W may be a tighter fit for this pocket. The interrelationship between these two residues in the Y- and F-containing copolymers provided herein is examined using copolymers synthesized at different ratios of Y:F. Further, V- and W-containing copolymers and V- and Y-containing copolymers, selected for synthesis on the basis of the need for differently sized aromatic groups to accommodate the differing sizes of the P1 and P4 pockets, are shown in Example 11 to be particularly effective in treating EAE symptoms. With present knowledge of the size, shape and charge distributions of each of the P1 and P4 pockets, and the data on V- and W-containing polymers as therapeutic agents for EAE, it is possible to design amino acids with novel organic side chains that could substitute for V and W, respectively, in synthesis of a copolymer, to provide an agent having an equivalent or even tighter fit of the side chain into these sites than V and W. A copolymer containing such a compound might be an even more useful therapeutic agent for an autoimmune disease such as EAE or MS.

The invention having now been fully described, additional embodiments of the invention can be found in the Examples and in the claims below, which embodiments are not to be construed as further limiting. The contents of each of the publications and patents cited are hereby incorporated in their entirety by reference herein.

EXAMPLES

Materials and Methods

Copolymers, peptides and antibodies. Poly (Y,E,A,K), referred to as YEAK, poly(V,E,A,K) or VEAK; and poly(F, E,A,K) or FEAK, in molar ratios approximating those found in Cop1 (wherein the V or F are present in the same molar ratio as the Y in Cop1), were synthesized by the solid phase method as 14-, 35- and 50-mers (Chiron Technologies, Clayton, Australia), by using fmoc amino acids mixed in the desired ratios at each cycle. Cop1 batch 52596, in the molar ratio of 1 Y:1.5 E:4.3 A:3.3 K (indicated herein as Y:E:A:K having a molar ratio of 1:1.5:4.4:3.3, with an average molecular weight (MW) of 8,150, (Teitelbaum D. et al. 1971. Eur. J. Immunol. 1:242-248), was obtained from Teva Pharmaceutical Industries (Petach Tiqva, Israel). Glatiramer acetate (Cop 1, Copaxone®) was obtained from Teva Marion Partners, Kansas City, Mo. Biotinylation of Cop1 was performed with excess N-hydroxysuccinimide biotin (Sigma) in DMSO as described (Fridkis-Hareli M. et al. 1994. Proc. Natl. Acad. Sci. USA 91:4872-4876). Unreacted biotin was removed by dialysis (Spectra/Por® membrane MWCO 500; Spectrum Medical Industries, Laguna Hills, Calif.).

Peptides were synthesized using solid phase techniques (Barany, G., and R. Merrifield. 1979. Academic Press, New York, N.Y.) on an Applied Biosystems Peptide Synthesizer and purified by reversed-phase HPLC(RP-HPLC). Peptide sequences were MBP (human basic myelin protein) 86-100, NPVVHFFKNIVTPRT (SEQ ID NO: 1); MBP 85-99, ENPVVHFFKNIVTPR (SEQ ID NO: 2), MW 1795; PLP (human proteolipid protein) 40-60, TGTEKLIETYF-SKNYQDYEYL (SEQ ID NO: 3), MW 2603; and mouse PLP 139-151, HSLGKWLGHPDKF (SEQ ID NO: 4), MW 1520, either unlabeled or labeled with biotin linked to the N-terminus by the spacer SGSG and free acid at the C-terminus.

Copolymers FAK (molar ratio 1:5:3), YFAK (molar ratio 0.2:0.8:5:3), YFAK (molar ratio 0.8:0.2:5:3) and YFAK (molar ratio 0.5:0.5:5:3) were synthesized by solid phase chemistry as 50-mers (Chiron Technologies, Clayton, Australia). A variance of about 10% from the input molar ratios and observed the amino acid compositions of the resulting polymers was found consistent with previously reported data from use of this procedure. Equivalent embodiments of the copolymers described herein can have molar ratios that vary about two-fold, about three-fold or about four-fold from those specified herein without substantial loss of pharmacological properties. Molar ratios that are about two-fold, about three-fold or about four-fold different from those used in the Examples, which merely illustrate the present invention and are not further limiting, are within the embodiments of the invention herein.

Protein expression and purification. Soluble HLA-DR-2 molecules were expressed in Drosophila S2 cells and purified as described (Kalandadze, A. et al. 1996. J. Biol. Chem. 271:20156-20162). Cells were grown at 26° C. in roller bottles in ExCell 401 medium (JRH Biosciences, Lenexa, Kans.) supplemented with 0-5% fetal bovine serum (Sigma Chemicals, St. Louis, Mo.). Cells were harvested 4-5 days after induction by 1 mM $CuSO_4$. Supernatant from harvested cells was sequentially passed through Protein A, Protein G and Protein A-LB3.1 columns, followed by elution of the bound HLA-DR with 50 mM 3-[cyclohexylamino]-1-propanesulfonic acid (CAPS), pH 11.5, and neutralized with 200 mM phosphate (pH 6.0). Proteins were concentrated on a Centriprep 10 membrane (Amicon, Beverly, Mass.).

HPLC separation and microsequencing. Different copolymers were separated and pool sequenced as previously described (Fridkis-Hareli, M. et al. 1999. J. Immunol. 162: 4697-4704). Briefly, the fractionation was by microbore HPLC using a C18 1.0 mm reverse-phase column (ZORBAX) on a Hewlett-Packard 1090 HPLC with 1040 diode array detector. Copolymers were eluted at a flow rate of 54 µl/min with a gradient of 0.055% trifluoroacetic acid (TFA) in acetonitrile (0% at 0 to 10 min, 33% at 73 min and 60% at 105 min) Strategies for peak selection, reverse phase separation and Edman microsequencing have been previously described (Chicz, R. M. et al. 1993. J. Exp Med. 178: 27-47). Pooled fractions were submitted to automated Edman degradation on a Hewlett-Packard G1005A (Palo Alto, Calif.) protein sequencer using the manufacturer's Routine 3.5.

Assays for Peptide Binding to Class II MHC Proteins.
(A). Solutions. The solutions used in this assay are the following: binding buffer is 20 mM 2-[N-morpholino]ethanesulfonic acid (MES), 140 mM NaCl, 0.05% NaN$_3$, pH 5.0, unless otherwise specified; PBS is 150 mM sodium chloride, 7.5 mM sodium phosphate, dibasic, 2.5 mM sodium phosphate, monobasic, pH 7.2; TBS is 137 mM sodium chloride, 25 mM Tris pH 8.0, 2.7 mM potassium chloride; TTBS is TBS plus 0.05% Tween-20.
(B). Microtiter assay plate preparation. Immunoassay plates (96-well microtiter, PRO-BIND™, Falcon, Lincoln Park, N.J.) were coated with 1 µg/well affinity-purified LB3.1 monoclonal antibodies in PBS (100 µl total) for 18 hrs at 4° C. The wells were then blocked with TBS/3% BSA for 1 hr at 37° C. and washed three times with TTBS. Before sample addition, 500 of TBS/1% BSA was added to each well.
(C). Inhibition reactions. Biotinylated peptide MBP 86-100 (SEQ ID NO: 1), final concentration 0.13 µM in 50 µl of the binding buffer, was co-incubated with unlabeled inhibitors (random copolymers or MBP 85-99, SEQ ID NO: 2), and HLA-DR-2 molecules for 40 hr at 37° C.
(D). Detection of class II MHC protein/peptide complexes. Bound peptide-biotin was detected using streptavidin-conjugated alkaline phosphatase, as follows. Plates were washed three times with TTBS and incubated with 100 µl of streptavidin-conjugated alkaline phosphatase (1:3000, BioRad, Richmond, Calif.) for 1 hr at 37° C., followed by addition of p-nitrophenyl phosphate in triethanolamine buffer (BioRad). Absorbance at 410 nm was monitored by a microplate reader (model MR4000; Dynatech, Chantilly, Va.).

Antigen presentation assays. HLA-DR-2-restricted T cells were MBP 84-102-specific transfectants carrying the genes for TCR obtained from patients with relapsing-remitting MS carrying DR-2 (8073, patient Ob (DRB1*1501) and Hy1B, patient Hy (DRB1*1602)), into BW 58 TCR $\alpha^-/\beta^-$ cells (Fridkis-Hareli, M. et al. 2001 Human Immunol. 62: 753-763); and MBP 84-102-specific (2E12) and PLP 40-60-specific (106A) hybridomas from HLA-DR-2-transgenic mice (Madsen, L. S. et al. 1999. Nat. Genet. 23:343-347). Mouse T cell hybridomas were PLP 139-151-specific H-2$^s$-restricted (hPLP/1 and hPLP/c4, Santambrogio, L. et al. 1993. J. Immunol. 151: 1116). Antigen presenting cells (APC) were L466 (L cells transfected with HLA-DR-2b (DRB1*1501)), L416 (L cells transfected with HLA-DR-2a (DRB5*0101)), MGAR (EBV-transformed B cells homozygous for DRB1*1501), and splenocytes from SJL/J (H-2$^s$) mice. T cell stimulation experiments were performed in a total volume of 200 µl in 96-well microtiter plates. Irradiated (3000 rad) APC (2.5×10$^4$/well) were co-incubated with MBP 85-99 (SEQ ID NO: 2), PLP 40-60 (SEQ ID NO: 3) or PLP 139-151 (SEQ ID NO: 4) and the random copolymers, at concentrations indicated, for 2 hr at 37° C. Then T cells (5×10$^4$/well) were added, and plates were incubated for 24 hr at 37° C. Supernatants (30 µl) were taken and were incubated with IL-2-dependent CTLL (5×10$^4$/well) for 12 hr, followed by labeling with $^3$H-thymidine (1 µCi/well) for 12 hr. Plates were harvested, and the radioactivity was monitored using a 1450 microbeta Plus liquid scintillation counter (Wallac, Gaithersburg, Md.).

Mouse strains. SJL/J (H-2$^s$) mice (8-12 weeks of age) were purchased from Jackson Laboratories (Bar Harbor, Me.) and were maintained in the animal facility at Harvard University according to the Guidelines of the Committee on Animals of Harvard University and the Committee on Care and Use of Laboratory Animal Resources, National Research Counsel (Department of Health and Human Services Publication 85-23, revised 1987). Humanized mice (Madsen, L. S. et al. 1999 Nat. Genet. 23(3): 343-347; and D. Altman, D. Hafler, and V. Kuchroo, unpublished) carry transgenes HLA DR-2 (DRA*0101 and DRB1*1501) and TCR from MS patient Ob, which is a V(D)J rearrangement of TCRα and TCRβ amplified from clone Ob.1A12.

Induction and suppression of EAE. Mice were injected subcutaneously both in the base of the tail and the nape of the neck with either whole spinal cord homogenate (WSCH, 500 µg/mouse, prepared as previously described (Santambrogio, L. et al. 1993. J. Immunol. 151:1116-1127), or with PLP 139-151 peptide (50 µg/mouse; SEQ ID NO:4) together with 400 µg Mycobacterium tuberculosis H37Ra (BD Difco Laboratories, Sparks, Md.) in an emulsion containing equal parts of PBS and complete Freund's adjuvant (CFA; Sigma Chemical Co., St. Louis, Mo.). Pertussis toxin (List Biological Laboratories, Campbell, Calif., 200 ng) was injected intravenously into the tail one day after immunization. Mice were scored daily for clinical signs of EAE on a scale 1-5, according to the severity of disease symptoms as previously described (Santambrogio, L. et al. 1993. J. Immunol. 151: 1116). For determination of suppression of EAE, each copolymer (500 µg/mouse) was mixed and injected with the encephalitogenic emulsion as described above.

Neuropathology. For assessment of inflammation and demyelination, mice were perfused under anesthesia through the ascending aorta with 40 ml of Trump's fixative (4% paraformaldehyde, 1% glutaraldehyde in 0.1 M phosphate buffer, pH 7.4). Slices of the brain and spinal cord were postfixed in cold 1% osmium tetroxide for 1 hr, were dehydrated through a graded series of solvents having increasing ethanol, and were embedded in epoxy resin. Sections of one µm were obtained, and were stained with toluidine blue and examined by light microscopy.

Example 1

Synthesis and Microchemical Analysis of Novel Copolymers

Random four-amino acid copolymers YEAK, VEAK, and FEAK, each of 14-, 35- and 50-mer in length, were synthesized by the solid phase method. V or F were chosen to be substituted for Y because of the following structural information: the P1 pocket of DRB1*1501 includes β86V resulting in a small pocket that can accommodate V or F but for which Y is too large to be accommodated (except at high peptide concentration; Krieger, J. I. et al. 1991. J. Immunol. 146: 2331-2340); the residue occurring at P1 in the binding of MBP 85-99 (SEQ ID NO: 2) is V, and F might provide a tighter fit; and the residue occurring at P4 in MBP 85-99 is F.

To determine whether the solid phase synthesis procedure yielded copolymers similar in amino acid composition, distribution, hydrophobicity and size, as compared to copolymer that had previously been generated only by solution chemistry, the novel compounds were subjected to amino acid analysis, RP-HPLC separation and microsequencing.

Amino acid analysis revealed molar ratios of Y, V, F, E and K in different copolymers to be similar to the predicted ratios, except for A, the molar ration of which was increased in all the copolymers, and particularly in the 35- and 50-mers. For example, in the 50-mer of VEAK, the molar ratios observed were 1.0 V: 2.1 E: 10.7 A: 2.9 K, as compared with the expected values of 1.0 V: 1.5 E: 5.0 A: 3.0 K. Separation of the copolymers by HPLC using an acetonitrile gradient showed a broad peak with several smaller peaks, which spread between about 40 and about 120 min elution time, similar to that of untreated Cop1 (Fridkis-Hareli, M., and J. L. Strominger 2001 *Hum. Immunol.* 62: 753-763). Edman sequencing of the first 10 amino acids showed constant ratios at each cycle, similar to those found by amino acid analysis, and indicating that the sequences of amino acids in the copolymers were random.

Example 2

Binding of the Novel Random Copolymers to HLA-DR-2 Molecules

Cop1 and certain three amino acid random copolymers synthesized in solution using N-carboxyamino acid anhydrides (Teitelbaum D. et al. 1971. *Eur. J. Immunol.* 1:242-248), viz., those containing three of the amino acids Y, E, A and K have been shown to bind to purified HLA-DR-2 and to compete for binding with MBP 85-99 (Fridkis-Hareli, M., and J. L. Strominger. 1998 *J. Immunol.* 160:4386-4397; Fridkis-Hareli, M. et al. 1999. *Int. Immunol.* 11:635-641).

To determine whether copolymers synthesized by the solid phase method also competed with this autoantigenic epitope for binding to HLA-DR-2, competitive binding assays were carried out with biotinylated MBP 86-100 (SEQ ID NO: 1) and the unlabeled peptides and random copolymers. Binding of biotinylated MBP 86-100 (SEQ ID NO: 1) to HLA-DR-2 molecules was inhibited most efficiently by the 50-mers of YEAK, the unlabeled MBP 85-99 (SEQ ID NO: 2) peptide or by Cop1. All other random copolymers tested here, i.e., those of 14 and 35 amino acid residues in length, were less effective in this assay.

Example 3

Proliferative Responses of MBP-specific T Cells in the Presence of the Random Copolymers A series of proliferation assays was performed to determine biological activity of each of the random copolymers with several MBP 84-102-specific T cell clones (see Materials and Methods).

Three types of APC, each expressing HLA-DR-2 molecules, were tested to determine which one presented the MBP 85-99 (SEQ ID NO: 2) peptide most efficiently. Higher levels of proliferation were observed when this peptide was presented by the human B cell line MGAR [DR-2b (DRB1*1501)-expressing] than by L466 (DR-2b-expressing L cell transfectant) cells. When L416 [DR-2a (DRB5*0101)-expressing L cells] were used, no response was detected, confirming that all the T cell clones were restricted to the DR-2b (DRB1*1501) allele. Therefore, MGAR cells, or sometimes L466 cells, were subsequently used in the antigen presentation assays described below.

The inhibition of proliferation in the presence of different copolymers of three different T cell clones by the MBP 85-99 peptide was examined. Generally, 14-mers were not inhibitory, regardless of the T cell clone tested, whereas 35- and 50-mers showed higher levels of inhibition. For all clones, YEAK 50-mer was approximately equivalent to Cop1 (which on average is a 70-mer) Inhibition fell off markedly with the YEAK 35-mer, and was very low with the YEAK 14-mer.

Figure 1C:
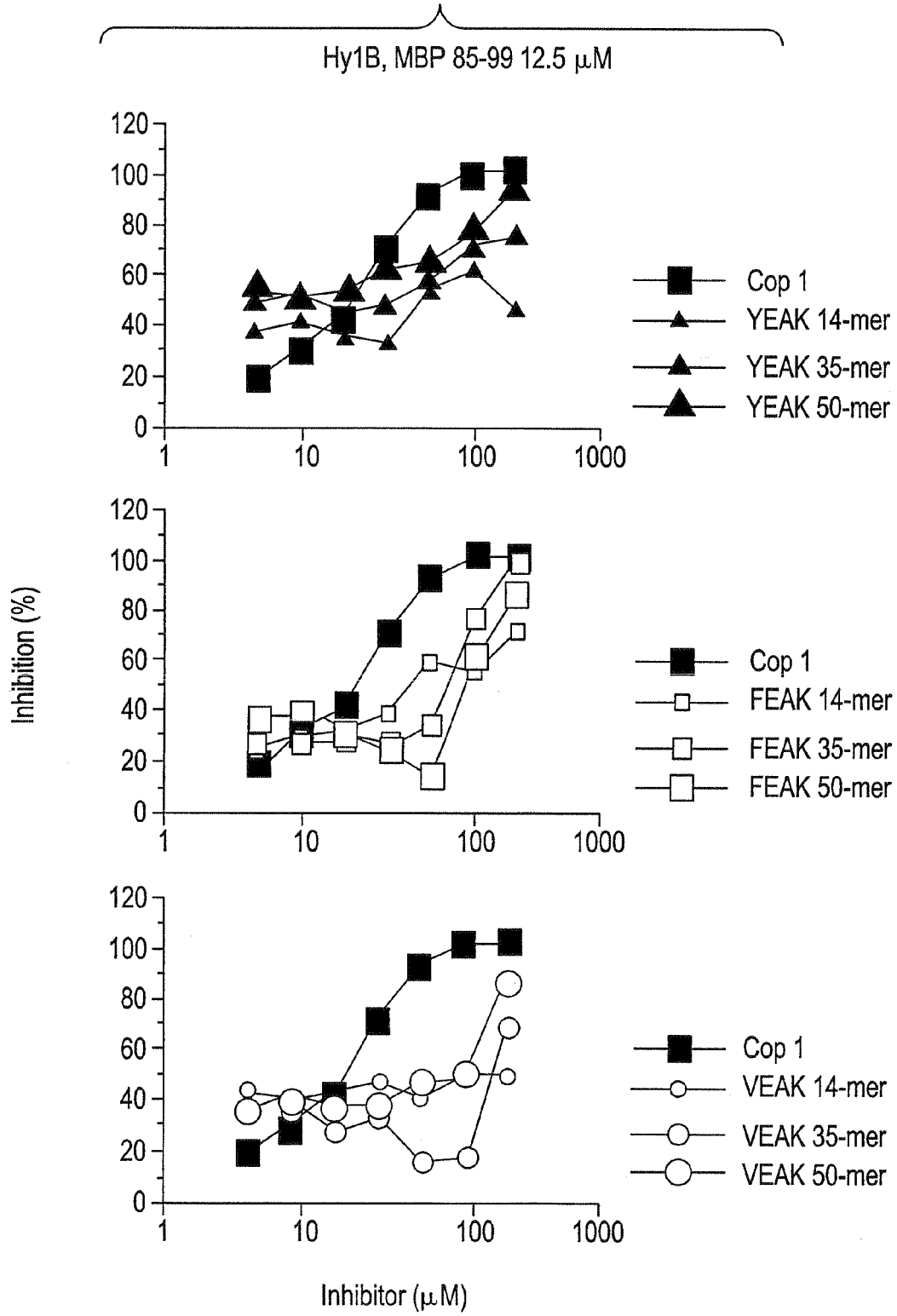

Inhibition of proliferation of the 2E12 T cell clone was efficient in the presence of the 35- and 50-mers of FEAK, and in the presence of Cop1 (FIG. 1A, lower left panel). VEAK did not inhibit the 2E12 clone (FIG. 1A, lower right panel). The 50-mer of FEAK was somewhat less inhibitory than Cop1. In the case of the Hy1B clone, Cop1 was the best inhibitor, and lower levels of inhibition by the 50-mers of FEAK and VEAK were observed (FIG. 1C).

The combination of V, E, A and K resulted in a low affinity binding to HLA-DR-2 molecules and low levels of inhibition of HLA-DR-2-restricted MBP 85-99-specific T cells. This is in despite the observation that in the MBP 85-99/HLA-DR-2 complex, V is the anchor residue at position 89 of the peptide (SEQ ID NO: 2), interacting with β86Val in the P1 pocket of the HLA-DR-2 protein (Smith, K. J. et al. 1998. *J. Exp. Med.* 19:1511-1520). The F side chain also fits in the P4 pocket, thus making the FEAK a better binding agent. Residue A may interact with the P1 pocket and Y with the P4 pocket (Smith, K. J. et al. 1998. *J. Exp. Med.* 19:1511-1520). MBP 85-99 (SEQ ID NO: 2) may be a relatively low affinity peptide because of V89.

Residue K in FEAK is most likely important for the interaction with the TCR, similarly to K at position 93 of MBP 85-99 (SEQ ID NO: 2; Wucherpfennig, K. W. et al. 1994. *J. Exp. Med.* 179:279-290; Smith, K. J. et al. 1998. *J. Exp. Med.* 19:1511-1520). On the other hand, K located near the N-terminus of the copolymer in the binding site may contribute to stable interactions with the HLA-DR molecules and the TCR, similarly to residue K at P-1 of HA 306-318 (SEQ ID NO: 5) bound to HLA-DR1 which can interact with the side chains of al helix residues at Sα53 or Eα55 (Stern, L. J. et al. 1994. *Nature* 368:215-221).

Example 4

Proliferation of PLP-specific T Cell Clones

To determine whether the random copolymers were able to inhibit the presentation of another potential autoantigen in MS, namely PLP, two different PLP epitopes were employed: human PLP 40-60 (SEQ ID NO: 3) that binds to DRB1*1501 (Krogsgaard, M. et al. 2000. *J. Exp. Med.* 191:1395-1412), and mouse PLP 139-151 (SEQ ID NO: 4) peptide that binds to H-2$^s$ and is encephalitogenic in SJL/J mice (Tuohy, V. K. et al. 1989 *J. Immunol.* 142:1523-1527). The T cells used in this assay were 106A (PLP 40-60-specific hybridomas from HLA-DR-2-transgenic mice; Madsen, L. S. et al. 1999. *Nat. Genet.* 23:343-347), and hPLP/1 and hPLP/c4 (PLP 139-151-specific H-2$^s$-restricted hybridomas from SJL/J mice; Santambrogio, L. et al. 1993. *J. Immunol.* 151:1116-1127). Proliferation of the T cell hybridomas was induced by the corresponding peptides in a dose-dependent manner. Each of the different copolymers was then added to the antigen presentation assay.

Presentation of the PLP 40-60 (SEQ ID NO: 3) epitope by the L466 APC to the 106A T cells was inhibited most efficiently by the 35- and 50-mers of FEAK (FIG. 2A, bottom panel). The levels of inhibition were somewhat higher than in the presence of Cop1. As in the case of the MBP-specific T cells, the YEAK 50-mer approximated Cop1 (FIG. 2A, top panel), while VEAK inhibited PLP 40-60-specific T cells only at the highest concentrations (FIG. 2A, middle panel).

Figure 2B:
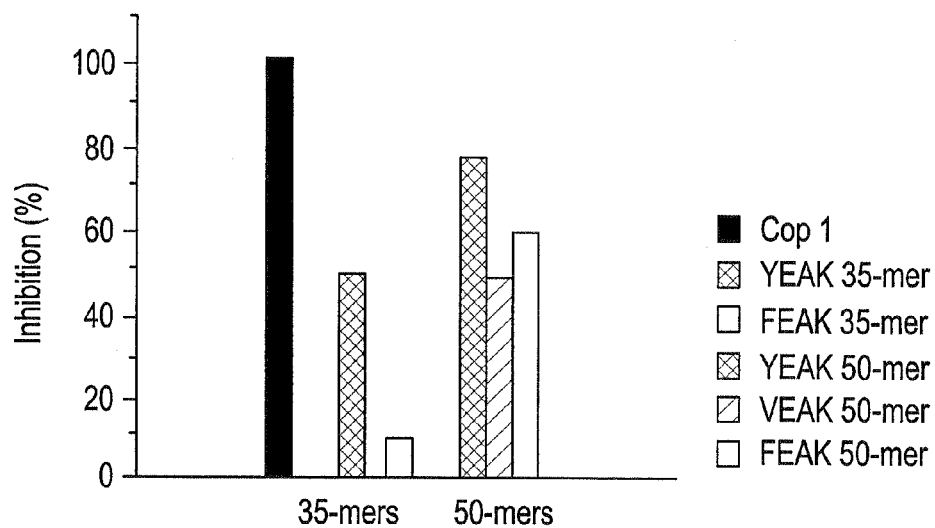
FIG. 2 is a set of line graphs (FIG. 2A) showing inhibition of HLA-DR-2-restricted PLP 40-60-specific human T cells 106 A, and a set of bar graphs (FIGS. 2B and 2C) showing inhibition of H-2$^s$-restricted PLP 139-151-specific mouse T cell hybridomas (hPLP/1 and hPLP/c4, respectively), in the presence of random copolymers. Irradiated L466 (FIG. 2A) or splenocytes from SJL/J (FIGS. 2B and 2C) mice were co-incubated with the proteolipid protein peptide PLP 40-60 (SEQ ID NO: 3) at a final concentration of 60 μM (A) and the concentrations of different copolymers as indicated on the abscissa, or with PLP 139-151 peptide (SEQ ID NO: 4; in B and C) at the final concentration of 24 μM, and the different copolymers (28 μM) for 2 hr at 37° C., then T cells were added and incubated for 24 hr at 37° C. Supernatants (30 μl) were incubated with IL-2-dependent CTLL, followed by labeling with $^3$H-thymidine (1 μCi/well) for 12 hr. * indicates 0% inhibition.
Figure 2C:
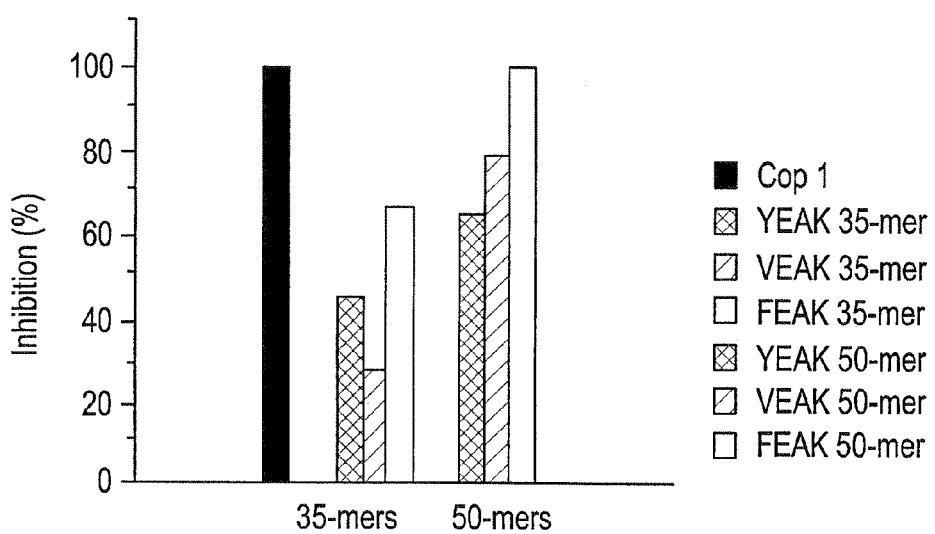

Proliferation of mouse H-2$^s$-restricted PLP 139-151-specific T cell hybridoma hPLP/1 was best inhibited by Cop1. FEAK or VEAK were somewhat less effective (FIG. 2B). The hPLP/c4 hybridoma was best inhibited by the 50-mers of FEAK and Cop1 (FIG. 2C).

Without being limited by any particular theory, several mechanisms have been postulated by which the copolymers may suppress a self-reactive T cell response: MHC/TCR blockage, competition, anergy induction, apoptosis, and bystander suppression. The first two mechanisms imply an effect of the copolymers on the early phase of the induction phase, when autoreactive T cells start expanding in number. Bystander suppression may act both on the induction and the effector phases, to promote development of regulatory T cells, or expansion of cross-reactive T cells and thereby suppress self-reactive encephalitogenic T cells. During ex-vivo proliferation, T cells of mice immunized with PLP 139-151 (SEQ ID NO: 4) developed a response only to the immunizing peptide, without any cross-reactivity to the tested copolymers. However when PLP 139-151 T cells were challenged in vitro in the presence both of the self-peptides and the copolymer, the response of the T cells to PLP 139-151 (SEQ ID NO: 4) was strongly abolished. Also, in several co-immunized mice, T cells proliferated in response to PLP139-151 (SEQ ID NO: 4) as well as to the copolymers.

The copolymers which when administered in vivo show greatest suppression of EAE in Examples below are also the best in suppressing T cell proliferative response to PLP 139-151 (SEQ ID NO: 4) in vitro. In such light, it appears that the more likely mechanism of action of the copolymers is blockage of MHC, and competition for antigen presentation.

Example 5

In vivo Effect of VEAK and FEAK Random Copolymers on EAE Induced by WSCH

To find out whether VEAK and FEAK random copolymers affected the clinical course of EAE in SJL/J mice, a number of in vivo experiments were performed. The protocol for disease induction was subcutaneous injection to co-immunize with both WSCH (500 μg) and each copolymer (500 μg), similar to the protocol of previous studies of suppression of EAE by Cop1 (Teitelbaum, D. et al. 1996. *J. Neuroimmunol.* 64:209-217). Following disease induction, mice were observed daily for 40 days for appearance of typical clinical signs of EAE (Table 1).

The data show that mice injected with WSCH developed EAE at around day 14-15 (Table 1, line 1) and had a maximal clinical score of about 2.2 (incidence: 18/32, mortality: 3%). Co-immunization with 35- or 50-mer VEAK (Table 1, lines 6 and 4, respectively) did not significantly affect the course of EAE, and resulted in an incidence and maximal score similar to the group injected with only WSCH, although in these co-immunized mice the onset of the disease may have been slightly delayed.

In contrast, mice treated with either 35-mer or 50-mer of FEAK (Table 1, lines 7 and 5 respectively) did not even develop symptoms of EAE. Treatment with Copaxone® (Table 1, line 2) suppressed EAE. One out of fourteen of the mice treated with Copaxone® developed the disease on day 20, with a maximal score of 3.0. Similarly, two out of sixteen mice injected with the 50-mer of YEAK (Table 1, line 3) developed mild EAE on day 14, with a maximal score of 1.0.

To determine the extent of inflammation and demyelination in mice injected with each of the different copolymers, central nervous system immunohistochemistry was performed on spinal cord samples. Samples from the lumbar cord of diseased mice injected with WSCH only, or with WSCH and VEAK 50-mer, showed extensive submeningeal, perivascular and parenchymal infiltration, as well as demyelination. In contrast, no symptoms of infiltration or demyelination were detected in samples from those mice that had not developed any signs of disease after treatment with the other copolymers.

Among different random copolymers synthesized and characterized in examples herein, FEAK was most efficient in suppression of EAE induced by WSCH.

Example 6

Treatment with VEAK or FEAK Random Copolymers of EAE Induced by PLP 139-151 Peptide (SEQ ID NO: 4).

To find out whether random copolymers provided herein might affect development of chronic-relapsing EAE, mice were injected subcutaneously with 50 μg of PLP 139-151 (SEQ ID NO: 4; the encephalitogenic epitope in the SJL/J strain) alone, or with 50 μg of PLP 139-151 (SEQ ID NO: 4) and 500 μg of the copolymer. Mice were examined on a daily basis for 90 days after the induction of the disease.

Figure 3A:
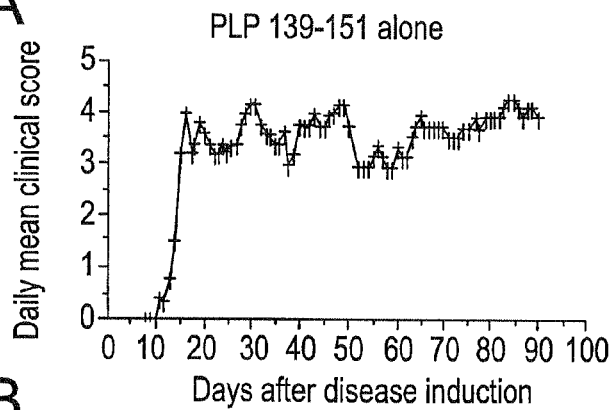
FIG. 3 is a set of graphs showing suppression by different random copolymers VEAK, FEAK, and Copaxone®, of EAE induced with PLP 139-151 (SEQ ID NO: 4) peptide. SJL/J mice were co-injected subcutaneously with 50 μg of PLP 139-151 (SEQ ID NO: 4) peptide and 500 μg of the indicated random copolymers, or with PLP 139-151 (SEQ ID NO: 4) alone. Progression of the disease was monitored for the appearance of clinical symptoms, scored on the ordinate, for the days shown on the abscissa. Results shown on the ordinate represent the mean daily score of clinical symptoms.

Immunization with the PLP 139-151 (SEQ ID NO: 4) epitope alone in CFA resulted in EAE with more severe clinical signs (FIG. 3A) compared to EAE induced by WSCH (Table 1). For example, five of eight mice developed severe symptoms of EAE with a mortality of 33%. The first attack occurred at about day 14 after immunization, with a maximal clinical score of 4.0, followed by subsequent fluctuation in disease attacks peaking approximately at days 30, 50, 70 and 85.

Figure 3B:
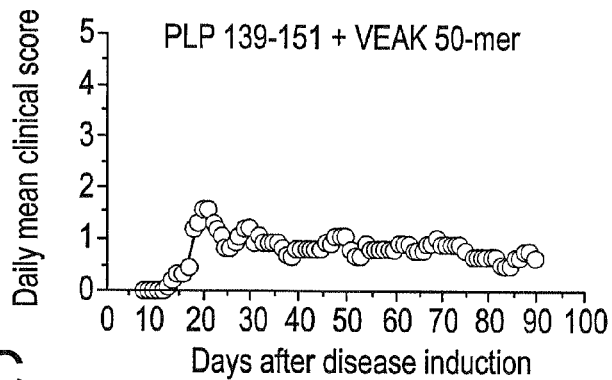

Co-injection with the various copolymers differentially reduced the clinical signs of EAE. In the VEAK 50-mer-treated group (FIG. 3B), four out of eight mice showed clinical signs of EAE (mortality: 12%). The first attack developed on day 13 and peaked at about day 20 (mean maximal score: 1.6).

Figure 3C:
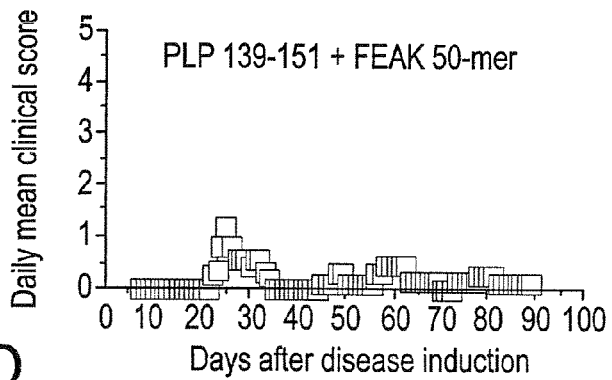

Co-injection with the FEAK 50-mer (FIG. 3C) resulted in three sick mice out of eight (mortality: 0%). The first attack was delayed and was less symptomatically severe (days 23-25, mean maximal score of 1.1) compared to the control receiving the peptide alone, or to the VEAK-treated group. Clinical symptoms were almost entirely remediated by about day 40.

Figure 3D:
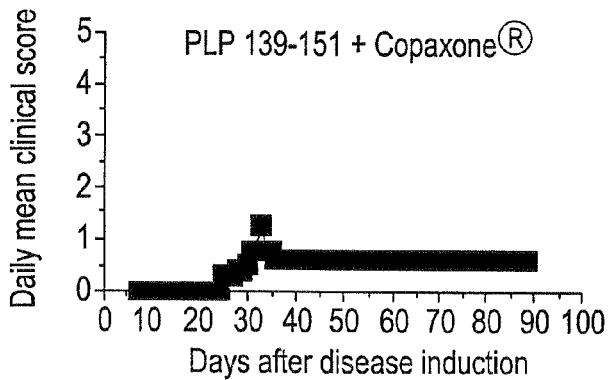
Figure 4:
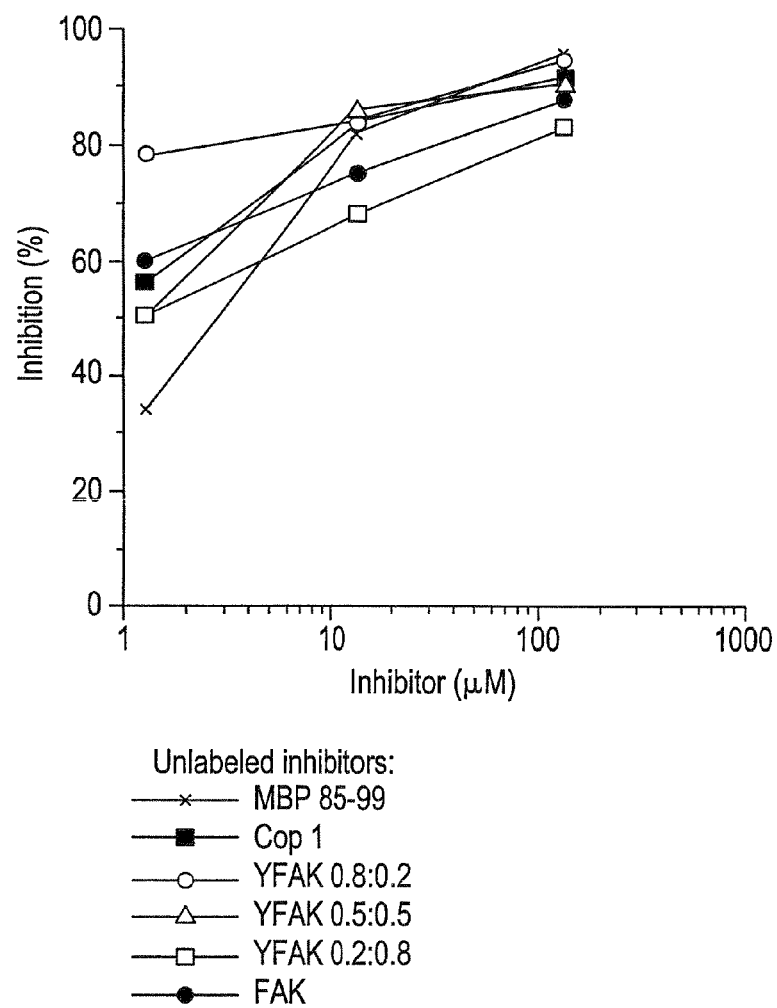
FIG. 4 is a graph showing inhibition of binding of biotinylated MBP 86-100 (SEQ ID NO: 1) to HLA-DR-2 molecules by random copolymers FAK, YFAK (0.8:0.2), YFAK (0.2:0.8), YFAK (0.5:0.5), and Cop 1. Recombinant water-soluble HLA-DR-2 molecules were incubated with biotinylated MBP 86-100 (SEQ ID NO: 1; 0.13 μM) and with the unlabeled random copolymers or the synthetic unlabeled peptide control MBP 85-99 (SEQ ID NO: 2), at concentrations shown on the abscissa. Incubations were carried out in duplicate at pH 7.0 for 40 hr at 37° C. Results shown as inhibition of binding on the ordinate represent one out of two independent experiments. Specific binding is expressed as percentage of inhibition using the formula: percentage of inhibition=100%−[(absorbance at 410 nm with competitor−background)/absorbance without competitor−background)×100]. The signals at 410 nm without competitor were 0.8-0.9 and the background was 0.1.
Figure 5:
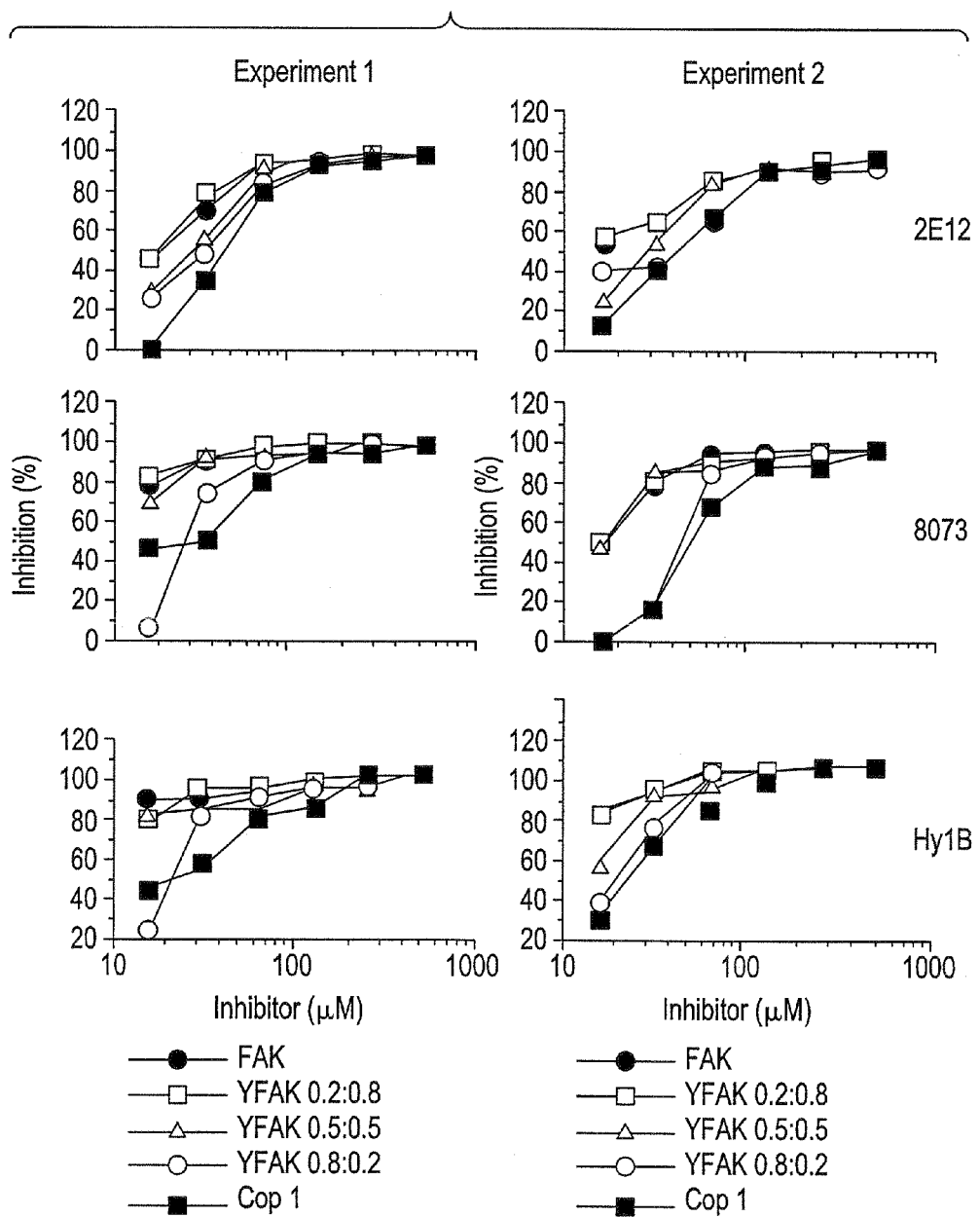
FIG. 5 is a set of graphs showing inhibition of HLA-DR-2-restricted MBP 84-102-specific T cells for each of cell lines 2E12, 8073 and Hy1B, in the presence of random copolymers FAK, YFAK (0.8:0.2), YFAK (0.2:0.8), YFAK (0.5:0.5), and Cop 1. Irradiated MGAR cells were co-incubated in duplicates with MBP 85-99 (SEQ ID NO: 2) at the final concentration of 12.5 μM and different concentrations of the random copolymers for 2 hr at 37° C., then T cells were added and incubated for 24 hr at 37° C. Supernatants (30 μl) were incubated with each of the IL-2-dependent CTLL cell lines as indicated, and were labeled with $^3$H-thymidine (1 μCi/well) for 12 hr.

Treatment with Copaxone® (FIG. 3D) led to delay of the first attack (starting on day 26, peak at day 34, maximal mean score: 1.25), similarly to results obtained with FEAK. In the Copaxone® group, two out of eight mice developed EAE with a mortality of 12%.

The data in Table 1 and FIG. 3 indicate that EAE induced by either WSCH or by PLP 139-151 (SEQ ID NO: 4) peptide was efficiently suppressed by the FEAK 50-mers. Further, these data demonstrate that 50-mers of FEAK suppressed EAE induced by either WSCH or the PLP 139-151 (SEQ ID NO: 4) peptide more efficiently than Cop1. This observation was evident when both the encephalitogenic material and the copolymer were injected simultaneously into SJL/J mice. Cop1 inhibits EAE induced by either WSCH or the synthetic PLP peptides, and interferes with PLP-specific T cell responses only when mice were co-immunized with both antigens (Teitelbaum, D. et al. 1996. *J. Neuroimmunol.* 64:209-217), suggesting that they compete for binding to class II MHC molecules.

Without being limited by any particular theory, the mechanism of activity of the 50-mer random copolymers provided herein might be similar to that of Cop1, leading to inhibition of binding of potential autoantigenic peptides to class II MHC proteins, and subsequent T cell suppression.

Example 7

Synthesis and Microchemical Analysis of Y- and F-containing Copolymers

It is shown supra that 50-mers compared to 14- or 35-mers of random copolymers composed of the amino acids Y, E, A and K are potent inhibitors of the binding of human immunodominant epitopes MBP 85-99 (SEQ ID NO: 2) to MS-associated HLA-DR-2 (DRB1*1501). Some of these copolymers inhibited the response of HLA DR-2-restricted MBP 84-102-specific T cells, and also suppressed EAE in the susceptible SJL/J strain induced by the encephalitogenic epitope PLP 139-151 (SEQ ID NO: 4).

Here, analysis of each of amino acid composition and amino acid ratios within the copolymers, is shown for random three-copolymer FAK 50-mer, and for the four-amino acid copolymer YFAK, at different ratios of Y:F (the "Y- and F-containing" polymers), each 50-mer copolymer synthesized as a 50-mer by the solid phase method. Amino acids that comprise these copolymers were chosen according to the anchor residues of the MBP 85-99 (SEQ ID NO: 2) epitope bound to HLA-DR-2 (DRB1*1501) molecules.

Copolymers having different ratios of Y and F were designed according to the following structural criteria: the P1 pocket of DRB1*1501 includes β86V resulting in a small pocket that can accommodate F but for which Y is too large to be accommodated; thus F would provide a tighter fit for P1 although the residue occurring at P1 in the binding of MBP 85-99 is V; and the residue occurring at P4 in MBP 85-99 is F, but this pocket is large enough to accommodate Y, which may be a better fit than F. To determine whether the synthesis procedure yielded substances similar in amino acid composition, distribution, hydrophobicity and size, as compared to those generated by previous techniques, the novel compounds were subjected to amino acid analysis, RP-HPLC separation and microsequencing.

Amino acid analysis revealed that the molar ratios of Y, F and K in each of the different copolymers were similar to the expected input molar ratios, except for A, the molar ratio of which was increased in all the copolymers. HPLC separation of the copolymers, using an acetonitrile gradient as previously described for Cop1 (Fridkis-Hareli, M. et al. (1999) J. Immunol. 162, 4697-4704), showed a broad peak with several smaller peaks, which eluted between about 40 and 80 min, similar to elution of untreated Cop1.

Pool sequencing of the first several amino acids of each copolymer synthesized here showed random patterns, with significantly higher levels of A over the levels of each of Y, F, or K, which corresponded to the initially higher molar ratio of A found by analyzing the composition of these random copolymers. No sequence specificity or preferential positioning of any amino acid in the copolymers was observed, indicating that the polymers were of random sequence.

Example 8

Binding of the Y- and F-containing Random Copolymers to HLA-DR-2 Molecules

To determine whether the Y- and F-containing copolymers synthesized herein by the solid phase method can compete with autoantigenic MS-associated epitope MBP 85-99 (SEQ ID NO: 2) for binding to HLA-DR-2 molecules, competitive binding assays were carried out with biotinylated MBP 86-100 (SEQ ID NO: 1) and each of the unlabeled random copolymers.

Binding of biotinylated MBP 86-100 (SEQ ID NO: 1) to HLA-DR-2 molecules was efficiently inhibited by FAK 50-mer and the YFAK 50-mer copolymer (having the molar ratio Y0.8:F0.2; FIG. 4). Thus, the Y- and F-containing 50-mer random copolymers herein compete with the MS-related epitope (SEQ ID NO: 1) for binding to MS-associated HLA-DR-2 molecules.

Example 9

Proliferative Responses of MBP-Specific T Cells in the Presence of the Random 50-mer Copolymers Effects of the presence of each of 50-mer copolymers FAK, YFAK (0.2:0.8), YFAK (0.5:0.5), and YFAK (0.8:0.2) on proliferation of three different T cell clones, in response to the MBP 85-99 (SEQ ID NO: 2) peptide, were examined, and results from two independent experiments are shown in FIG. 5.

The data show that for each of three MBP-specific HLA-DR-2-restricted clones, the three Y- and F-containing YFAK copolymers and the FAK copolymer were efficient inhibitors. Among these copolymers, YFAK 0.2:0.8, YFAK 0.5:0.5, and FAK were better inhibitors than YFAK 0.8:0.2, and were superior to Cop 1.

The superior inhibitor activities of the three YFAK copolymers having different Y:F ratios and of the FAK copolymer were observed at lower concentrations (e.g., at about 20 μM) of each of these better inhibitors for clone 2E12, and at several low copolymer concentrations with the other T cell clones. At higher concentrations, e.g., greater than about 100 μM, the observed levels of inhibition were similar for all of the copolymers tested in this example (FIG. 5).

Example 10

Treatment of EAE Induced by PLP 139-151 (SEQ ID NO: 4) with Y- and F-containing Copolymers In vivo experiments were carried out to determine whether the Y- and F-containing 50-mer random copolymers would affect the clinical course of EAE in SJL/J mice. As in Examples above, the protocol for co-immunization was subcutaneous injection of SJL/J mice with, in this example, the encephalitogenic epitope PLP 139-151 (SEQ ID NO: 4; 50 μg) and a copolymer preparation (500 μg). Following disease induction, mice were observed daily for appearance of typical signs of EAE, during a period of 70 days.

Immunization with PLP 139-151 (SEQ ID NO: 4) epitope alone in CFA resulted in chronic-relapsing EAE (FIG. 6; Table 2). All 13 mice receiving this treatment developed severe EAE, with a mortality of 77%. The first signs appeared around day 11, followed by subsequent fluctuation in disease attacks, with a mean maximal score of 4.6 (FIG. 6).

Figure 6B:
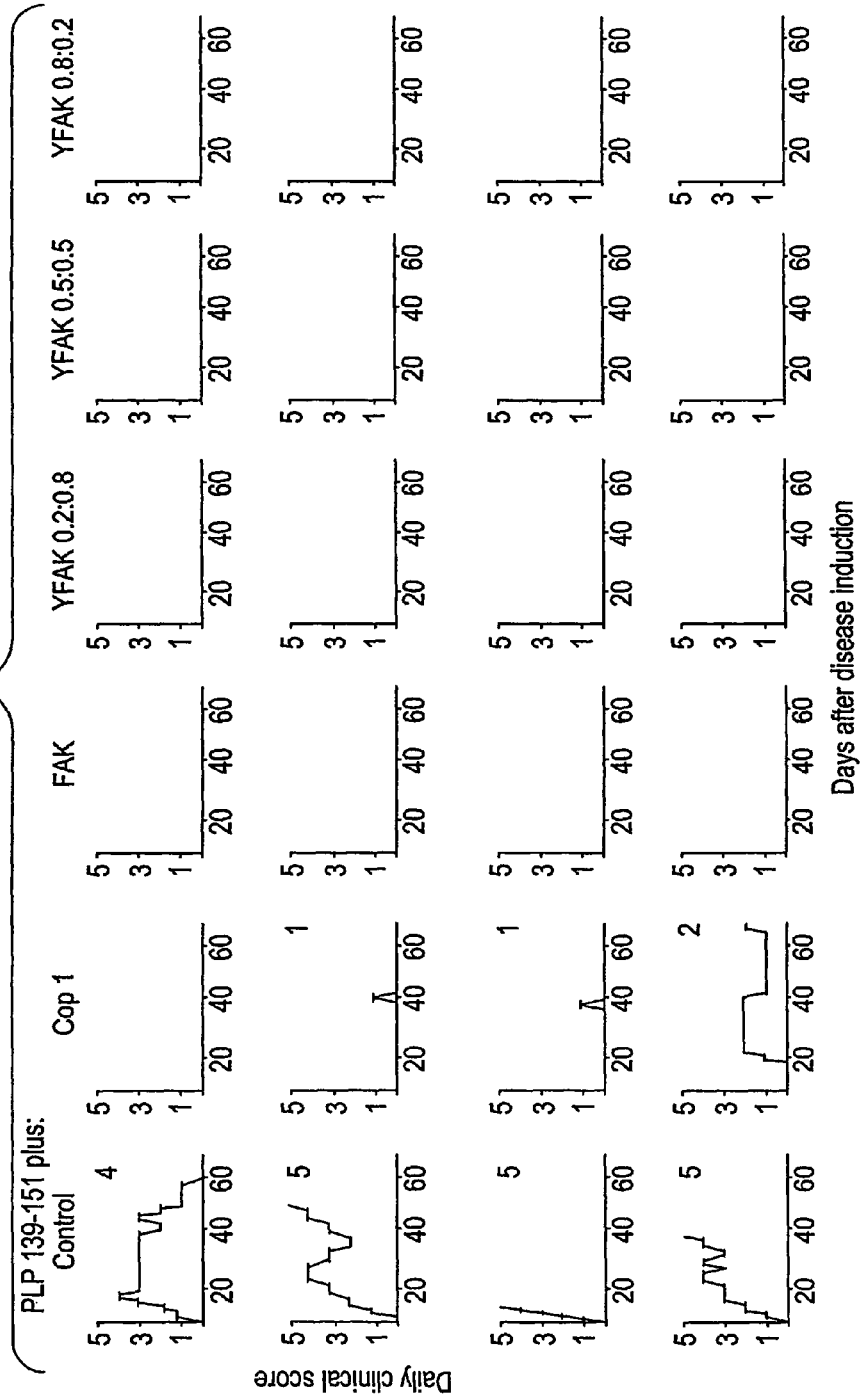
FIG. 6B shows data for each individual mouse, with the copolymer treatment of the group listed at the top of each column, and the maximal clinical score observed for the mouse indicated in the upper right hand corner of each box, for a representative experiment.

Co-injection of random copolymers herein differentially reduced the clinical signs of EAE. In the YFAK 0.2:0.8-treated group, only two out of 16 mice showed clinical signs of EAE (mortality: 6%), and these clinical signs occurred with a delay in the first attack which occurred about day 37 (mean maximal score: 0.6; FIG. 6, Table 2) rather than day 11 as in the untreated group.

Similarly, in the YFAK 0.5:0.5-treated group, one sick mouse of 16 was observed (mortality: 0%), with the first attack developing on day 33. Further, of mice treated with YFAK 0.8:0.2, eight of 17 developed EAE, with no mortality. In this group, the observed mean maximal clinical score of 1.5 and the time of onset (day 27) were each indicative of a less therapeutic benefit than these data obtained for mice treated with the YFAK preparations having the lower ratios of Y to F shown above.

Co-injection with FAK resulted in three sick mice of 17, with 12% mortality, mean maximal score of 0.9 and mean onset of day 25 (Table 2, line 5). Copaxone® co-injected with PLP 139-151 (SEQ ID NO: 4), resulted in 12 of 16 mice developing EAE, with mean onset at day 22, and a mean clinical score of 2.6 (Table 2, line 6).

Observation of clinical symptoms in individual mice in another experiment (FIG. 6B) shows that YFAK 0.5:0.5 treatment eliminated all symptoms in the entire group of mice treated with this copolymer. From these data on individual mice, it is clear that F-containing copolymers are more effective in remediation of PLP-induced EAE than Cop 1, and that a greater molar ratio of F to Y is associated with superior remediation of EAE.

In summary, EAE induced by PLP 139-151 (SEQ ID NO: 4) was efficiently suppressed by the three different YFAK copolymers and by FAK, with the order of efficacy being YFAK 0.5:0.5>YFAK 0.2:0.8>FAK>YFAK 0.8:0.2. The F-containing copolymers remediated PLP-induced EAE more effectively than Cop 1.

The Y- and F-containing random amino acid copolymers synthesized and analyzed herein are more potent in binding to HLA-DR-2 molecules, inhibition of autoantigen-specific T cells, and suppression of EAE, than Cop 1 (Copaxone®). These copolymers were designed and synthesized mainly based on those residues of immunodominant T cell epitope MBP 85-99 (SEQ ID NO:2) interacting with the MS-associated HLA-DR-2 (DRB1*1501) molecules. The length of the copolymer preparations is shown herein to be important for activity, with the 50-mers being most efficient. Longer polypeptides may be able to link adjacent class II molecules.

The 50-mer random copolymer FAK and the YFAK 50-mer copolymers of different molar ratios of Y to F herein are more potent than control Copaxone® in the following functional activities: binding to HLA-DR-2 molecules, inhibition of MBP-specific DR-2-restricted T cells, and suppression of EAE. Random copolymer VEAK showed low affinity binding to HLA-DR-2 molecules, low levels of inhibition of HLA-DR-2-restricted MBP 85-99-specific T cells and no effect on progression of EAE, in spite of having an amino acid residue V at a position that is equivalent to the P1 of the MBP 85-99 auto antigen (SEQ ID NO: 2). Data herein show that substitution of V by F resulted in a better inhibitory compound, probably due to a tighter fit of F into the P1 pocket, and Y into the P4 pocket.

Most significant is the effect of the copolymers herein on progression of EAE induced by encephalitogenic epitope PLP 139-151 (SEQ ID NO: 4). Clinical signs of EAE were significantly reduced by treatment with the YFAK copolymers or with FAK, when the encephalitogenic material and the copolymer were injected simultaneously into SJL/J mice.

Without being limited by any particular theory, these data support a mechanism of activity of the random copolymers involving the copolymers as efficient blockers of antigen presentation by class II MHC molecules, leading to inhibition of binding of the potential autoantigenic peptides and subsequent autoimmune T cell suppression.

The YFAK 50-mer and FAK 50-mer copolymers are candidates for use in treatment of MS, a disease in which 60% of the patients are of HLA-DR-2 (DRB1*1501) haplotype. Given the promiscuous binding abilities of random copolymers (Fridkis-Hareli, M., et al. 1998 *J. Immunol.* 160: 4386-4397; Fridkis-Hareli, M. et al. 1999 *Int. Immunol:* 635-641), the copolymers herein may be beneficial also in MS patients having other HLA-DR specificities, and might provide new therapeutic compounds for use in other autoimmune conditions.

Example 11

Co/Pre-immunization Treatment with Valine (V)- and Tyrosine (Y)- or Valine (V)- and Tryptophan- (W)-containing Copolymers Suppresses MBP 85-99 (SEQ ID NO: 2) Induced EAE in Humanized Mice The peptide-binding pockets of HLA-DR-2 DRB1*1501 have a β86 Val residue at P1, and is of a size that can accommodate a residue which is a V or F, but not of sufficient size to accommodate a Y or W. In contrast, the large hydrophobic pocket P4 contains a β71 Ala, therefore it can accommodate a residue of large size such as Y or W; and the P9 pocket is promiscuous. Based on these structural considerations, copolymers containing valine (V) and tyrosine (Y), or valine (V) and tryptophan (W), along with A and K, were synthesized and tested for effect on progression and symptoms of EAE induced by MBP 85-99 (SEQ ID NO: 2).

Figure 7:
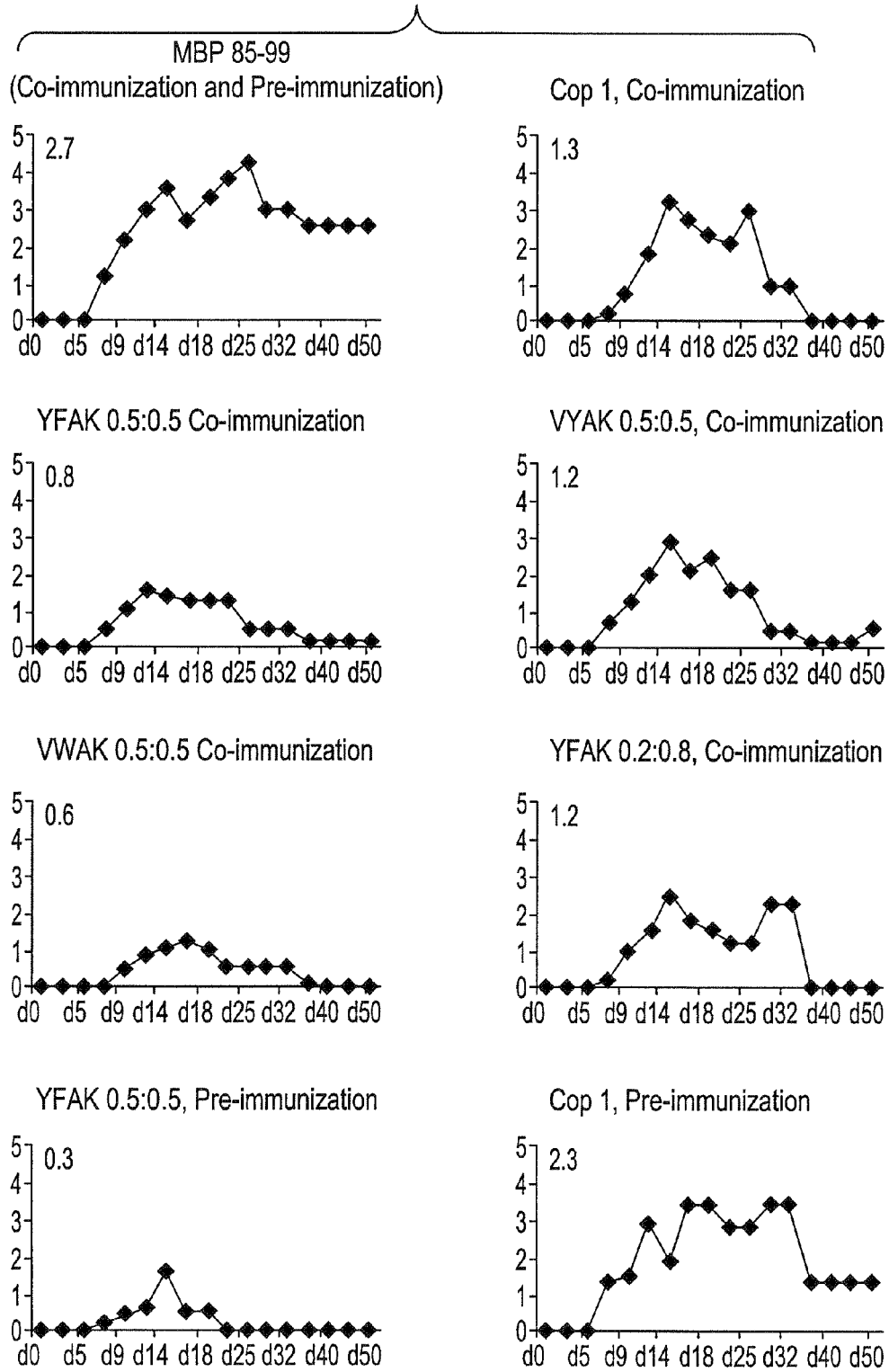
FIG. 7 is a set of line graphs showing suppression, by different random copolymers YFAK, VWAK, VWAK, or Cop 1, of EAE induced with MBP 85-89 (SEQ ID NO: 2) peptide, and control mice not treated with copolymer. Humanized mice (Madsen, L. S. et al. 1999 Nat. Genet. 23(3): 343-347; and D. Altman, D. Hafler, and V. Kuchroo, unpublished) carry transgenes HLA DR-2 (DRA*0101 and DRB1*1501) and TCR from MS patient Ob, which is a V(D)J rearrangement of TCRα and TCRβ amplified from clone Ob.1A12. Co-immunized mice were co-injected on day 0 with 500 μg of the copolymer or control material as indicated, and 50 μg of the EAE inducing peptide MBP 85-89 (SEQ ID NO: 2). Pre-immunized mice were preinjected with the copolymer two days prior to EAE induction. The copolymers VYAK and VWAK respectively, have molar ratios of 0.5:0.5:5:3 of V:Y:A:K and of V:W:A:K, respectively. The data points indicate progression of the disease by scoring of clinical symptoms, on the ordinate, on each of days 3, 5, 7, 9, 11, 14, 16, 18, 22, 25, 28, 32, 37, 40, 43 and 50, on the abscissa.

Experimental animals were humanized mice carrying transgenes HLA DR-2 (DRA*0101 and DRB1*1501) and TCR from MS patient Ob, which is a V(D)J rearrangement of TCRα and TCRβ, amplified from clone Ob.1A12. Mice in each group were injected with MBP 85-99 (SEQ ID NO: 2) subcutaneously to induce EAE. As shown in FIG. 7, groups of mice were pre-immunized with a single injection two days prior to EAE induction, either with Cop1, YFAK 0.5:0.5, or control MBP 85-89, or were simultaneously co-immunized with Cop1, YFAK 0.5:0.5, YFAK 0.2:0.8, VYAK 0.5:0.5, or with VWAK 0.5:0.5, and with the EAE-inducing MBP 85-99 (SEQ ID NO: 2). Clinical symptoms were monitored over a course of 50 days on days indicated.

Mice in the control group that were induced with MBP 85-99 (SEQ ID NO: 2) and otherwise untreated showed a severity of symptoms that exceeded a clinical score of 4 at about day 25. Clinical symptoms in this group generally rose to a high level of 3-4 for eight time points (days 11 to 32), prior to stabilizing at a level of severity between 2 and 3. Duration of symptoms was observed over a total of 14 time points (corresponding to day 7 to the end of the observation period, day 50), with symptoms stabilizing at between 2 and 3 in severity.

In contrast, mice induced with MBP 85-99 (SEQ ID NO: 2) and co-immunized with VWAK showed minimal EAE clinical symptoms (FIG. 7). During the 50 day course of the experiment, the mice exhibited a return to a normal clinical appearance by day 37. The symptoms recorded for VWAK-treated mice that appeared at about day 9 were observed at a greatest clinical score of about or less than about 1. Other copolymers shown in FIG. 7, while providing some symptom remediation compared to the MBP 85-99 (SEQ ID NO: 2) control, did not so substantially reduce the severity of symptoms, which ranged from 1 to slightly above 2 (for the group co-immunized with YFAK 0.2:0.8), 1 to 2 (for the group pre-immunized with YFAK 0.5:0.5), and slightly greater than 1 (for the group co immunized with YFAK 0.5:0.5).

Figure 8:
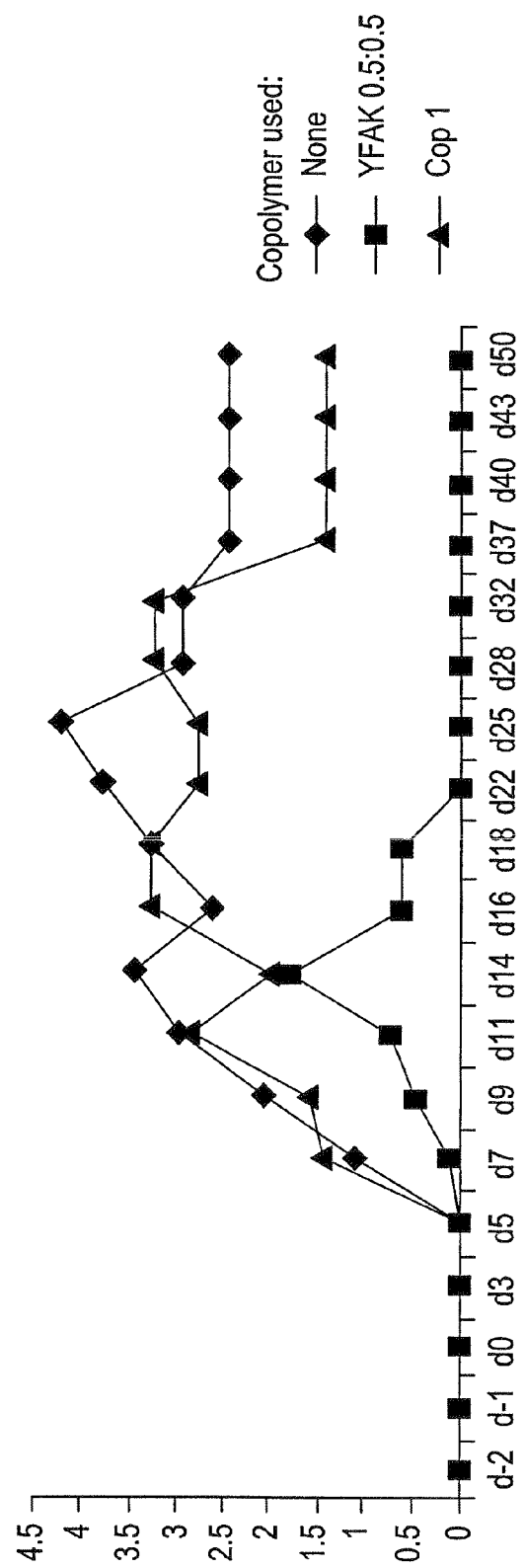
FIG. 8 is a set of line graphs, replotted together from data for three of the groups of animals from FIG. 7: diamonds are control EAE-induced mice not further receiving copolymer treatment; squares are EAE-induced mice treated with YFAK 0.5:0.5; and triangles are EAE-induced mice treated with Cop1. Each treatment in this figure was administered two days prior to EAE induction, i.e., vaccination against disease.

The greatest remediation of symptoms was found in the group that was co-immunized with VWAK, and the shortest duration of symptoms was found in the group that was pre-immunized with YFAK 0.5:0.5. In the latter group, symptoms were observed for a total of only five time points, followed by disappearance of clinical symptoms. The YFAK 0.5:0.5 pre-treatment data are co-plotted in FIG. 8 (square symbols) to show the contrasts in severity and duration of symptoms of the YFAK 0.5:0.5-treated group with the control group of MBP 85-99 (SEQ ID NO: 2; diamond-shaped symbols) induced and otherwise untreated, and the Cop1-treated group (FIG. 8, triangular symbols). The pre-immunization protocol used here is equivalent to vaccination against the autoimmune disease EAE.

In contrast to pre-immunization with YFAK 0.5:0.5, Cop1 pre-immunization or co-immunization in the same assay, while remediating symptoms, provided relief of symptoms to a level of a clinical score of about 2 to 3 (Cop1 co-immunization), or slightly greater than 3 (Cop1 pre-immunization). Further, symptoms were observed for nine time points, taken from days 7 through 37 (Cop1 co-immunization) prior to mice becoming asymptomatic, or over a period of 14 time points from days 7 through 50 (Cop1 pre-immunization), with mice achieving a stable level of symptoms of greater than about 1 in severity, rather than elimination of symptoms as in the YFAK-treated group. These data show that YFAK 0.5:0.5 is most effective in pre-immunization of animals against development of the EAE disease condition.

These data indicate that the presence of W or F in a random copolymer with amino acids V, A, and K may increase tightness of fit of the copolymer into a position of the class II MHC major groove, for example, into both the P1 and the P4 position. The data show that YFAK and VWAK are promising potential therapeutic agents for MS, for demyelinating conditions, and possibly for other autoimmune diseases.

TABLE 1

Clinical EAE Induced by WSH in Mice Injected with Different Random Copolymers

| Copolymer | Incidence[a] | Percent disease[b] | Percent mortality[c] | Maximum mean score[d] | Mean day of onset[d] |
|---|---|---|---|---|---|
| — | 18/32 | 56 | 3 | 2.2 ± 1.2 | 14.5 ± 2.3 |
| Copaxone ® | 1/14 | 7 | 0 | 3.0 | 20.0 |
| YEAR 50-mer | 2/16 | 12 | 0 | 1.0 | 14.0 |
| VEAK 50-mer | 8/16 | 50 | 0 | 2.8 ± 0.4 | 18.3 ± 7.4 |
| FEAK 50-mer | 0/16 | 0 | 0 | — | — |
| VEAK 35-mer | 3/9 | 30 | 0 | 1.5 ± 0.5 | 19.0 ± 3.0 |
| FEAK 35-mer | 0/10 | 0 | 0 | — | — |

Suppression of EAE induced with WSCH by the random copolymers in SJL/J mice. Mice were coinjected with 500 µg of WSCH and different random copolymers (500 µg), as described in Materials and Methods.

[a]Values represent the number of mice with clinical signs of EAE as a fraction of total number of immunized mice.

[b]Values represent the percentage of mice with clinical signs of disease.

[c]Values represent the percentage of mortality as referred to the total number of immunized mice.

[d]Values representing maximum clinical score and mean day of onset were calculated as described in Falk, O. et al. 2000 *J.Exp. Med.* 191:717-730.

TABLE 2

Clinical EAE Induced by PLP 139-151 in Mice Injected with Different Random Copolymers

| Copolymer | Incidence[a] | Percent[b] disease | Percent[c] mortality | Maximum[d] mean score | Mean day[d] of onset |
|---|---|---|---|---|---|
| — | 13/13 | 100 | 77 | 4.6 ± 0.8 | 11.5 ± 1.7 |
| YFAK 0.2:0.8 | 2/16 | 13 | 6 | 0.6 ± 1.5 | 37.5 ± 7.7 |
| YFAK 0.5:0.5 | 1/16 | 6 | 0 | 0.2 ± 1.0 | 33.0 ± 0 |
| YFAK 0.8:0.2 | 8/17 | 47 | 0 | 1.5 ± 1.7 | 26.6 ± 10.7 |
| FAK | 3/17 | 18 | 12 | 0.9 ± 1.8 | 25.0 ± 15.0 |
| Copaxone ® | 12/16 | 75 | 6 | 2.6 ± 1.6 | 22.7 ± 7.1 |

Suppression of EAE induced with PLP 139-151 epitope by the random copolymers in SJL/J mice. Mice were co-injected with 50 µg of PLP 139-151 and different random copolymers (500 µg), as described in Materials and Methods.

[a]Values represent the number of mice with clinical signs of EAE as a fraction of total number of immunized mice.

[b]Values represent the percentage of mice with clinical signs of disease.

[c]Values represent the percentage of mortality as referred to the total number of immunized mice.

[d]Values representing maximum clinical score and mean day of onset were calculated as described in Falk, O. et al. 2000. *J.Exp.Med.* 191:717-730.

What is claimed is:

1. A linear random copolymer FAK comprising amino acids phenylalanine (F), alanine (A), and lysine (K), wherein the amino acids F:A:K are polymerized in a molar ration having a range of 1:5:3 to 1:10:3.

2. A random linear copolymer comprising amino acids alanine (A), lysine (K), and a plurality of hydrophobic amino acids selected from the group consisting of: valine (V), phenylalanine (F), tryptophan (W), and tyrosine (Y), providing that the copolymer is not YFAK.

3. A composition comprising a copolymer according to claim 2 in combination with at least one additional therapeutic agent.

4. A composition according to claim 3, wherein the additional therapeutic agent is selected from the group of: an antibody, an enzyme inhibitor, an antibacterial, an antiviral, a steroid, a nonsteroidal anti-inflammatory, an antimetabolite, a cytokine, a cytokine blocking agent, an adhesion molecule blocking agent, and a soluble cytokine receptor.

5. A kit comprising at least one unit dosage of a random linear copolymer according to claim 2.

6. A kit according to claim 5, wherein the molar ratio in the copolymer of the amino acids A:K:(sum of the hydrophobic amino acids) has a range of about 5:3:1 to about 10:3:1.

* * * * *

UNITED STATES PATENT AND TRADEMARK OFFICE
CERTIFICATE OF CORRECTION

| | | |
|---|---|---|
| PATENT NO. | : 9,028,835 B2 | Page 1 of 1 |
| APPLICATION NO. | : 13/181079 | |
| DATED | : May 12, 2015 | |
| INVENTOR(S) | : Strominger et al. | |

It is certified that error appears in the above-identified patent and that said Letters Patent is hereby corrected as shown below:

In the Claims

At column 33, line 11:

delete "ration"

insert --ratio--

Signed and Sealed this
Twenty-second Day of September, 2015

Michelle K. Lee
*Director of the United States Patent and Trademark Office*

UNITED STATES PATENT AND TRADEMARK OFFICE
CERTIFICATE OF CORRECTION

| | | |
|---|---|---|
| PATENT NO. | : 9,028,835 B2 | Page 1 of 1 |
| APPLICATION NO. | : 13/181079 | |
| DATED | : May 12, 2015 | |
| INVENTOR(S) | : Strominger et al. | |

It is certified that error appears in the above-identified patent and that said Letters Patent is hereby corrected as shown below:

In the Specification

Column 1, Lines 23-26:
Delete, "This invention was made in part with government support under grants CA47554 and AI49524 awarded by the National Institutes of Health. The government has certain rights in the invention."

And insert -- This invention was made with government support under CA047554 and AI049524 awarded by the National Institutes of Health. The government has certain rights in the invention. --

Signed and Sealed this
Fourth Day of August, 2020

Andrei Iancu
*Director of the United States Patent and Trademark Office*